(12) United States Patent
Vidlund et al.

(10) Patent No.: US 11,612,480 B2
(45) Date of Patent: Mar. 28, 2023

(54) EPICARDIAL ANCHOR DEVICES AND METHODS

(71) Applicant: Tendyne Holdings, Inc., St. Paul, MN (US)

(72) Inventors: Robert M. Vidlund, Forest Lake, MN (US); Mark Christianson, Plymouth, MN (US); Craig Ekvall, East Bethel, MN (US)

(73) Assignee: Tendyne Holdings, inc., St. Paul, MN (US)

( * ) Notice: Subject to any disclaimer, the term of this patent is extended or adjusted under 35 U.S.C. 154(b) by 478 days.

(21) Appl. No.: 16/790,875

(22) Filed: Feb. 14, 2020

(65) Prior Publication Data
US 2020/0179112 A1    Jun. 11, 2020

Related U.S. Application Data

(60) Division of application No. 15/001,727, filed on Jan. 20, 2016, now Pat. No. 10,610,354, which is a
(Continued)

(51) Int. Cl.
*A61F 2/24* (2006.01)
*A61B 17/04* (2006.01)
(Continued)

(52) U.S. Cl.
CPC ........ *A61F 2/2418* (2013.01); *A61B 17/0057* (2013.01); *A61B 17/0401* (2013.01);
(Continued)

(58) Field of Classification Search
CPC ...... A61B 17/0057; A61B 2017/00243; A61B 2017/0448; A61B 17/0487;
(Continued)

(56) References Cited

U.S. PATENT DOCUMENTS 2,697,008 A    12/1954  Ross
3,409,013 A    11/1968  Berry
(Continued)

FOREIGN PATENT DOCUMENTS

CN    1486161 A    3/2004
CN    1961845 A    5/2007
(Continued)

OTHER PUBLICATIONS

US 9,155,620 B2, 10/2015, Gross et al. (withdrawn)
(Continued)

*Primary Examiner* — Brian E Pellegrino
(74) *Attorney, Agent, or Firm* — Wei & Sleman LLP

(57) ABSTRACT

Apparatus and methods are described herein for anchoring a prosthetic heart valve. In some embodiments, an apparatus includes a tether attachment member that includes a base member that defines at least a portion of a tether passageway through which a portion of a tether extending from a prosthetic heart valve can be received therethrough. The base member defines a locking pin channel that intersects the tether passageway. A locking pin is disposable within the locking pin channel and movable between a first position in which the locking pin is at a spaced distance from the tether passageway, and a second position in which the locking pin intersects the tether passageway and can engage the portion of a tether disposed therein to secure the tether to the tether attachment member.

17 Claims, 31 Drawing Sheets

Related U.S. Application Data continuation of application No. PCT/US2014/049218, filed on Jul. 31, 2014, which is a continuation-in-part of application No. 14/224,764, filed on Mar. 25, 2014, now abandoned.

(60) Provisional application No. 61/895,975, filed on Oct. 25, 2013, provisional application No. 61/861,356, filed on Aug. 1, 2013.

(51) Int. Cl.
  *A61B 17/00* (2006.01)
  *A61B 90/00* (2016.01)

(52) U.S. Cl.
  CPC .. *A61B 17/0487* (2013.01); *A61B 2017/0061* (2013.01); *A61B 2017/00243* (2013.01); *A61B 2017/00477* (2013.01); *A61B 2017/00575* (2013.01); *A61B 2017/0404* (2013.01); *A61B 2017/0409* (2013.01); *A61B 2017/0414* (2013.01); *A61B 2017/0417* (2013.01); *A61B 2017/0448* (2013.01); *A61B 2017/0453* (2013.01); *A61B 2017/0464* (2013.01); *A61B 2090/3966* (2016.02); *A61F 2/2457* (2013.01); *A61F 2220/0008* (2013.01); *A61F 2230/0069* (2013.01)

(58) Field of Classification Search
  CPC ..... A61B 2017/0451; A61B 2017/0409; A61F 2/2457; A61F 2220/0008
  See application file for complete search history.

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,858,810 A | 8/1989 | Intlekofer et al. |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,578,076 A | 11/1996 | Krueger et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |

(56) References Cited

U.S. PATENT DOCUMENTS

| | | |
|---|---|---|
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |

(56) References Cited

U.S. PATENT DOCUMENTS

| | | |
|---|---|---|
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 3,007,992 A1 | 8/2011 | Tian et al. |
| 7,988,727 B2 | 8/2011 | Santamore et al. |
| 7,993,394 B2 | 8/2011 | Hariton et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,625,003 B2 | 4/2017 | Hooti et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Altieri et al. |
| 2005/0075727 A1 | 4/2005 | Wheatley |
| 2005/0080402 A1 | 4/2005 | Santamore et al. |
| 2005/0085900 A1 | 4/2005 | Case et al. |

(56) References Cited

U.S. PATENT DOCUMENTS

| | | |
|---|---|---|
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |

(56) References Cited

U.S. PATENT DOCUMENTS

| | | |
|---|---|---|
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1* | 1/2013 | Rowe ............... A61F 2/2487 600/16 |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0158600 A1 | 6/2013 | Conklin et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |
| 2015/0223934 A1 | 8/2015 | Vidlund et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |

(56) References Cited

U.S. PATENT DOCUMENTS

| | | |
|---|---|---|
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0193138 A1 | 7/2018 | Vidlund |
| 2018/0263618 A1 | 9/2018 | Vidlund et al. |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101984938 A | 3/2011 |
| CN | 102869317 A | 1/2013 |
| CN | 102869318 A | 1/2013 |
| CN | 102869321 A | 1/2013 |
| CN | 103220993 A | 7/2013 |
| CN | 102639179 B | 10/2014 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |
| JP | 2005515836 A | 6/2005 |
| JP | 2009514628 A | 4/2009 |
| JP | 2009519783 A | 5/2009 |
| JP | 2013512765 A | 4/2013 |
| NL | 1017275 C2 | 8/2002 |
| SU | 1271508 A1 | 11/1986 |
| WO | 9217118 A1 | 10/1992 |
| WO | 9301768 A1 | 2/1993 |
| WO | 9829057 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 2000041652 | 7/2000 |
| WO | 2000047139 A1 | 8/2000 |
| WO | 2001035878 A2 | 5/2001 |
| WO | 200149213 A3 | 7/2001 |
| WO | 0154625 A1 | 8/2001 |
| WO | 2001054624 A1 | 8/2001 |
| WO | 2001056512 A1 | 8/2001 |
| WO | 2001061289 A1 | 8/2001 |
| WO | 2001076510 A2 | 10/2001 |
| WO | 2001082840 A1 | 11/2001 |
| WO | 2002004757 A1 | 1/2002 |
| WO | 2002022054 A1 | 3/2002 |
| WO | 2002028321 A2 | 4/2002 |
| WO | 2002036048 A1 | 5/2002 |
| WO | 2002041789 A2 | 5/2002 |
| WO | 2002043620 A1 | 6/2002 |
| WO | 2002049540 A2 | 6/2002 |
| WO | 2002076348 A1 | 10/2002 |
| WO | 2003003943 A2 | 1/2003 |
| WO | 2003030776 A2 | 4/2003 |
| WO | 03047468 A1 | 6/2003 |
| WO | 2003049619 A2 | 6/2003 |
| WO | 2004019825 A1 | 3/2004 |
| WO | 2005102181 A1 | 11/2005 |
| WO | 2006014233 A2 | 2/2006 |
| WO | 2006034008 A2 | 3/2006 |
| WO | 2006064490 A1 | 6/2006 |
| WO | 2006070372 A2 | 7/2006 |
| WO | 2006105009 A1 | 10/2006 |
| WO | 2006113906 A1 | 10/2006 |
| WO | 2006127756 A2 | 11/2006 |
| WO | 2007081412 A1 | 7/2007 |
| WO | 2007100408 A2 | 9/2007 |
| WO | 2008005405 A1 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009132187 A1 | 10/2009 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | WO-2011072084 A2 * | 6/2011 ........... A61F 2/2418 |
| WO | 2011106735 A1 | 9/2011 |
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012095116 A1 | 7/2012 |
| WO | 2012177942 A2 | 12/2012 |
| WO | 2013045262 A1 | 4/2013 |
| WO | 2013059747 A1 | 4/2013 |
| WO | 2013096411 A1 | 6/2013 |
| WO | 2013175468 A2 | 11/2013 |
| WO | 2014121280 A2 | 8/2014 |
| WO | 2014144937 A2 | 9/2014 |
| WO | 2014162306 A2 | 10/2014 |

(56) References Cited

FOREIGN PATENT DOCUMENTS

| | | | |
|---|---|---|---|
| WO | 2014189974 A1 | 11/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |
| WO | 2015138306 A2 | 9/2015 |
| WO | 2015173609 A1 | 11/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |
| WO | 2017096157 A1 | 6/2017 |
| WO | 2017132008 A1 | 8/2017 |
| WO | 2017218375 A1 | 12/2017 |
| WO | 2018005779 A1 | 1/2018 |
| WO | 2018013515 A1 | 1/2018 |

OTHER PUBLICATIONS

Webb, J. G. et al., "Percutaneous Aortic Valve Implantation Retrograde from the Femoral Artery," Circulation, 2006, 113:842-850.
Wheatley, M.D., David J., "Valve Prostheses," Rob & Smith's Operative Surgery, Fourth Edition, pp. 415-424, ButtenNorths 1986.
Yoganathan, A. P. et al., "The Current Status of Prosthetic Heart Valves," In Polymetric Materials and Artificial Organs, Mar. 20, 1983, pp. 111-150, American Chemical Society.
"Shape Memory Alloys," Retrieved from the Internet: <http://webdocs.cs.ualberta.ca/~database/MEMS/sma.html>, Feb. 5, 2016, 3 pages.
Al Zaibag, Muayed, et al., "Percutaneous Balloon Valvotomy in Tricuspid Stenos's," British Heart Journal, Jan. 1987, vol. 57, No. 1, pp. 51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration In Dilated Hearts," Interactive Cardiovascular and Thoracic Surgery, 2005, 4:475-477.
Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Examination Report No. 1 for Australian Application No. 2014296087, dated Aug. 22, 2018, 5 pages.
G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.
Gray, H., The Aorta, Anatomy of the Human Body, 1918, Retrieved from the Internet <http://www.bartleby.com/107/142.html>, Dec. 10, 2012, 5 pages.
Gray, H., The Heart, Anatomy of the Human Body, 1918, Retrieved from the Internet <http://education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.
Inoue, K. et al., "Clinical Application of Transvenous Mitral Commissurotomy by a New Balloon Catheter," The Journal of Thoracic and Cardiovascular Surgery, 1984, 87:394-402.
International Search Report and Written Opinion for International Application No. PCT/US2014/049218, dated Oct. 20, 2014, 14 pages.
Jin, X. Y. et al., "Aortic Root Geometry and Stentless Porcine Valve Competence," Seminars in Thoracic and Cardiovascular Surgery, Oct. 1999, 11(4):145-150.
Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991,retrieved from the Internet on Feb. 5, 2016, 3 pages.
L. L. Knudsen et al., "Catheter-Implanted Prosthetic Heart Valves. Transluminal Catheter Implantation of a New Expandable Artificial Heart Valve in the Descending Thoracic Aorta in Isolated Vessels and Closed Chest Pigs," International Journal of Artificial Organs, 1993, Issue 5, vol. 16, pp. 253-262.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutter, Georg, et al., Mitral valved stent implantation, European Journal of Cardio-Thoracic Surgery, 2010, vol. 38, pp. 350-355.
Ma, L. et al., "Double-crowned valved stents for off-pump mitral valve replacement," European Journal of Cardio-Thoracic Surgery, Aug. 2005, 28(2): 194-198.
Moazami, N. et al., "Transluminal aortic valve placement: A feasibility study with a newly designed collapsible aortic valve," ASAIO Journal, Sep./Oct. 1996, 42(5):M381-M385.
Office Action for Chinese Application No. 201480050061.7, dated Feb. 3, 2017, 21 pages.
Office Action for Japanese Application No. 2016-531904, dated May 1, 2018, 11 pages.
Office Action for U.S. Appl. No. 14/224,764, dated Jul. 31, 2015, 9 pages.
Orton, C., "Mitralseal: Hybrid Transcatheter Mitral Valve Replacement," Symposium: Small Animal Proceedings, 2011, pp. 311-312.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Porstmann, W. et al., "Der Verschluß des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196( 11 ): 173-174.
Rashkind, W. J., "Historical Aspects of Interventional Cardiology: Past, Present, Future," Texas Heart Institute Journal, Dec. 1986, 13(4):363-367.
Reul, H. et al., "The Geomety of the Aortic Root in Health, at Valve Disease and After Valve Replacement," J. Biomechanics, 1990, 23(2):181-191.

(56) References Cited

OTHER PUBLICATIONS

Robert C. Ashton Jr., "Development of an Intraluminal Device for the Treatment of Aortic Regurgitation: Prototype and n Vitro Testing System," Journal of Thoracic and Cardiovascular Surgery, 1996, Issue/vol. 112, pp. 979-983.
Rosch, J. et al., "The Birth, Eady Years and Future of Interventional Radiology," J Vasc Interv Radiol., Jul. 2003, 4:841-853.
Ross, D. N., "Aortic Valve Surgery," Guys Hospital, London, 1968, pp. 192-197.
Rousseau, E. P. M. et al., "A Mechanical Analysis of the Closed Hancock Heart Valve Prosthesis," Journal of Biomechanics, 1998, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Tofeig, M. et al., "Transcatheter Closure of a Mid-Muscular Ventricular Septal Defect with an Amplatzer VSD Occluder Device," Heart, 1999, 81:438-440.
Uchida, Barry T., et al., "Modifications of Gianturco Expandable Wire Stents," AJR:150, May 1988, Dec. 3, 1987, pp. 1185-1187.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.

\* cited by examiner

EPICARDIAL ANCHOR DEVICES AND METHODS

CROSS-REFERENCE TO RELATED APPLICATIONS

This application is a divisional of U.S. patent application Ser. No. 15/001,727, filed Jan. 20, 2016, which is continuation under 35 U.S.C. § 120 of International Application No. PCT/US2014/049218, filed Jul. 31, 2014, entitled "Epicardial Anchor Devices and Methods," which claims priority to and the benefit of U.S. Provisional Patent Application No. 61/861,356, filed Aug. 1, 2013, entitled "Pursestring Epicardial Pad Device," and U.S. Provisional Patent Application No. 61/895,975, filed Oct. 25, 2013, entitled "Improved Epicardial Pad Device," each of the disclosures of which is incorporated herein by reference in its entirety. International Application No. PCT/US2014/049218 is also a continuation-in-part of U.S. patent application Ser. No. 14/224,764, filed Mar. 25, 2014, entitled "Pursestring Epicardial Pad Device," which claims priority to and the benefit of U.S. Provisional Patent Application No. 61/861,356, filed Aug. 1, 2013, entitled "Pursestring Epicardial Pad Device," each of the disclosures of which is incorporated herein by reference in its entirety.

BACKGROUND

Embodiments are described herein that relate to devices and methods for anchoring a medical device such as a prosthetic heart valve replacement.

Some known devices for anchoring a medical device, such as, for example, a prosthetic heart valve (e.g. mitral valve) can include securing one or more tethers extending from the medical device to body tissue. For example, one or more tethers can extend from a prosthetic heart valve through an opening in the ventricular wall of the heart. Some known methods of anchoring or securing the tethers can include the use of staples or other fasteners that engage or pierce tissue near the puncture site. Such devices can have relatively large profiles and be difficult to easily deliver percutaneously to the desired anchoring site. Some known methods of securing a prosthetic heart valve can include suturing the tethers extending from the valve to body tissue, or tying the suture ends. Such devices and methods can be difficult to maneuver to secure the tether(s) with a desired tension, Further, when an opening is made directly into the ventricular wall or apex of a heart, such as when a prosthetic valve is percutaneously delivered and deployed, in addition to securing the prosthetic valve in a proper position, the efficacy of sealing the puncture site is critical to the life of the patient since hemodynamic losses from a cardiac puncture can cause shock and death within minutes. Further, the outward pressure that the puncture site is subjected to when it is located in the heart muscle itself is much higher than puncture sites that are distal to the heart. Accordingly, improved devices and methods for securing a prosthetic heart valve and for engaging and closing tissue, e.g., to close a cardiac puncture site, would be considered useful to solve these and other problems known in the art.

SUMMARY

Apparatus and methods for anchoring a prosthetic heart valve are described herein. In some embodiments, an apparatus includes a tether attachment member that includes a base member that defines at least a portion of a tether passageway through which a portion of a tether extending from a prosthetic heart valve can be received therethrough. The base member defines a locking pin channel that intersects the tether passageway. A locking pin is disposable within the locking pin channel and movable between a first position in which the locking pin is at a spaced distance from the tether passageway, and a second position in which the locking pin intersects the tether passageway and can engage the portion of a tether disposed therein to secure the tether to the tether attachment member.

DETAILED DESCRIPTION

Figure 1:
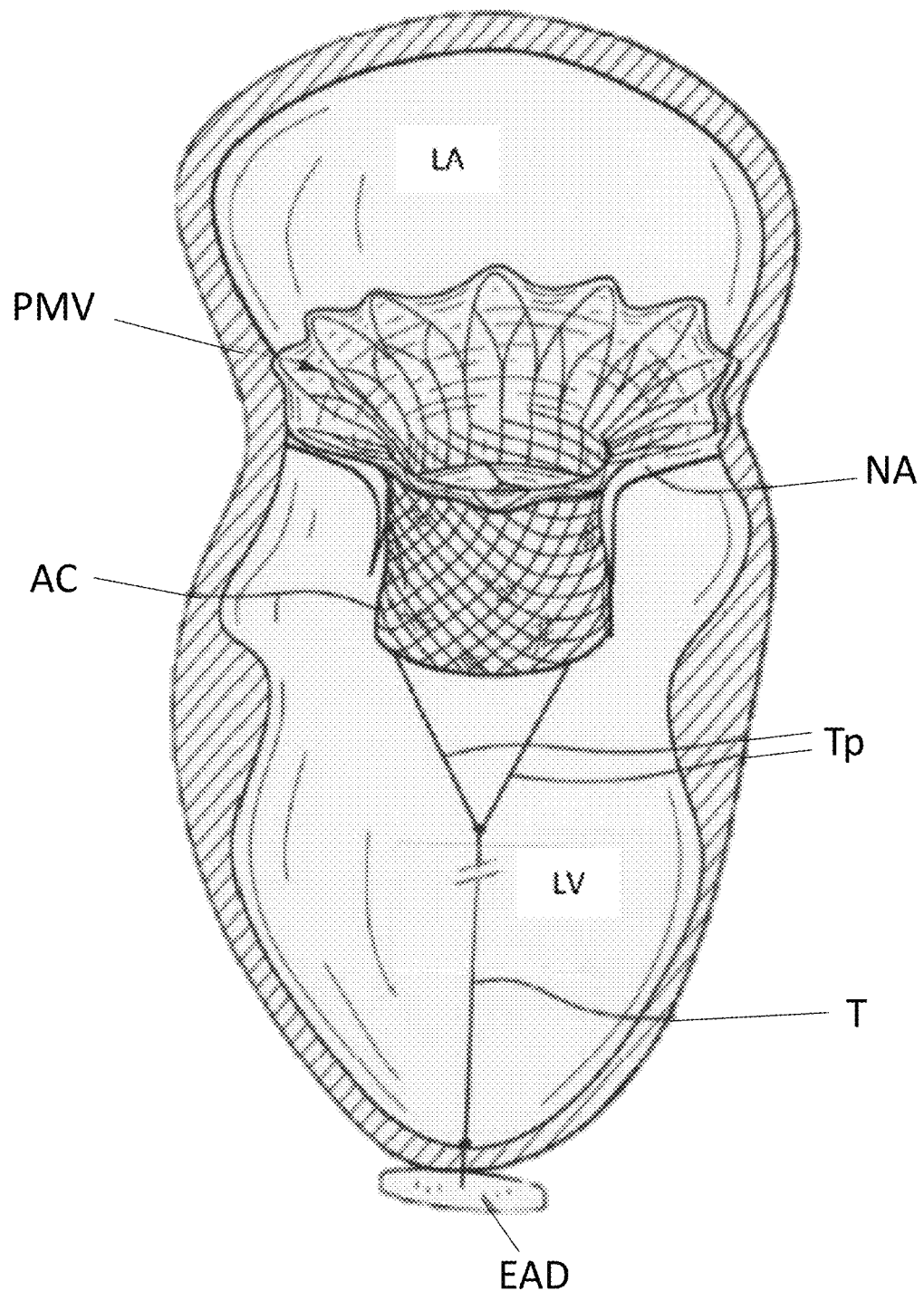
FIG. 1 is a cross-sectional illustration of portion of a heart with a prosthetic mitral valve implanted therein and an epicardial anchor device anchoring the mitral valve in position.

Apparatus and methods are described herein that can be used for securing and anchoring a prosthetic heart valve, such as, for example, a prosthetic mitral valve. Apparatus and methods described herein can also be used to close openings through the heart formed for example, when performing a procedure to implant a prosthetic heart valve. Apparatus and methods described herein can also be used to anchor other medical devices and/or to close punctures or openings in other body lumens formed during a diagnostic or therapeutic procedure.

In some embodiments, an apparatus includes a tether attachment member that includes a base member that defines at least a portion of a tether passageway through which a portion of a tether extending from a prosthetic heart valve can be received therethrough. The base member defines a locking pin channel that intersects the tether passageway. A locking pin is disposable within the locking pin channel and movable between a first position in which the locking pin is at a spaced distance from the tether passageway, and a second position in which the locking pin intersects the tether passageway and can engage the portion of a tether disposed therein to secure the tether to the tether attachment member.

In some embodiments, an apparatus includes a tether attachment member that includes a base member and a lever arm movably coupled to the base member. The base member and the lever arm collectively define a tether passageway through which a portion of a tether extending from a prosthetic heart valve can be received therethrough. The base member defines a locking pin channel that intersects the tether passageway and is in fluid communication therewith, and a locking pin is disposed within the locking pin channel. The lever arm is configured to be moved from a first position in which the portion of the tether can be inserted into the tether passageway, and a second position in which the locking pin secures a tether disposed within the tether passageway to the tether attachment member.

In some embodiments, an apparatus includes a tether attachment member that includes a base member and a hub member rotatably coupled to the base member. The base member and the hub each define at least a portion of a tether passageway through which a portion of a tether extending from a prosthetic heart valve can be received therethrough. The base member defines a locking pin channel that intersects the tether passageway and is in fluid communication therewith and a locking pin is disposed at least partially within the locking pin channel. The hub defines a cam channel in which a driver portion of the locking pin is received. The hub is configured to rotate relative to the base member such that the cam channel moves the locking pin linearly within the locking pin channel moving the locking pin from a first position in which the locking pin is at a spaced distance from the tether passageway, and a second position in which the locking pin intersects the tether passageway and engages a portion of a tether disposed therein to secure the tether to the tether attachment member.

In some embodiments, a method includes inserting into a tether passageway defined by a tether attachment member, a portion of a tether extending from a prosthetic heart valve. The tether attachment member is disposed adjacent an opening in a ventricular wall of a heart from which the tether extends. The tether attachment member is actuated such that a locking pin disposed within a locking pin channel defined by the tether attachment member intersects the tether passageway and engages a portion of the tether disposed within the tether passageway, securing the tether to the tether attachment member.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to a direction closer to and away from, respectively, an operator of, for example, a medical device. Thus, for example, the end of the medical device closest to the patient's body (e.g., contacting the patient's body or disposed within the patient's body) would be the distal end of the medical device, while the end opposite the distal end and closest to, for example, the user (or hand of the user) of the medical device, would be the proximal end of the medical device.

In some embodiments, an epicardial pad system is described herein that can be used to anchor a compressible prosthetic heart valve replacement (e.g., a prosthetic mitral valve), which can be deployed into a closed beating heart using a transcatheter delivery system. Such an adjustable-tether and epicardial pad system can be deployed via a minimally invasive procedure such as, for example, a procedure utilizing the intercostal or subxyphoid space for valve introduction. In such a procedure, the prosthetic valve can be formed in such a manner that it can be compressed to fit within a delivery system and secondarily ejected from the delivery system into the target location, for example, the mitral or tricuspid valve annulus.

A compressible prosthetic mitral valve can have a shape, for example that features a tubular stent body that contains leaflets and an atrial cuff. This allows the valve to seat within the mitral annulus and be held by the native mitral leaflets. The use of a flexible valve attached using an apical tether can provide compliance with the motion and geometry of the heart. The geometry and motion of the heart are well-known as exhibiting a complicated biphasic left ventricular deformation with muscle thickening and a sequential twisting motion. The additional use of the apically secured ventricular tether helps maintain the prosthetic valve's annular position without allowing the valve to migrate, while providing enough tension between the cuff and the atrial trabeculations to reduce, and preferably eliminate, perivalvular leaking. The use of a compliant valve prosthesis and the special shape and features can help reduce or eliminate clotting and hemodynamic issues, including left ventricular outflow tract (LVOT) interference problems. Many known valves are not able to address problems with blood flow and aorta/aortic valve compression issues.

Structurally, the prosthetic heart valve can include: a self-expanding tubular frame having a cuff at one end (the atrial end); one or more attachment points to which one or more tethers can be attached, preferably at or near the ventricular end of the valve; and a leaflet assembly that contains the valve leaflets, which can be formed from stabilized tissue or other suitable biological or synthetic material. In one embodiment, the leaflet assembly may include a wire form where a formed wire structure is used in conjunction with stabilized tissue to create a leaflet support structure, which can have anywhere from 1, 2, 3 or 4 leaflets, or valve cusps disposed therein. In another embodiment, the leaflet assembly can be wireless and use only the stabilized tissue and stent body to provide the leaflet support structure, and which can also have anywhere from 1, 2, 3 or 4 leaflets, or valve cusps disposed therein.

The upper cuff portion may be formed by heat-forming a portion of a tubular nitinol structure (formed from, for example, braided wire or a laser-cut tube) such that the lower portion retains the tubular shape but the upper portion is opened out of the tubular shape and expanded to create a widened collar structure that may be shaped in a variety of functional regular or irregular funnel-like or collar-like shapes.

A prosthetic mitral valve can be anchored to the heart at a location external to the heart via one or more tethers coupled to an anchor device, as described herein. For example, the tether(s) can be coupled to the prosthetic mitral valve and extend out of the heart and be secured at an exterior location (e.g., the epicardial surface) with an anchor device, as described herein. An anchor device as described herein can be used with one or more such tethers in other surgical situations where such a tether may be desired to extend from an intraluminal cavity to an external anchoring site.

FIG. 1 is a cross-sectional illustration of the left ventricle LV and left atrium LA of a heart having a transcatheter prosthetic mitral valve PMV deployed therein and an epicardial anchor device EAD as described herein securing the prosthetic mitral valve PMV in place. FIG. 1 illustrates the prosthetic mitral valve PMV seated into the native valve annulus and held there using an atrial cuff AC of the prosthetic mitral valve PMV, the radial tension from the native leaflets, and a ventricular tether T secured with attachment portions Tp to the prosthetic mitral valve PMV and to the epicardial anchor EAD. Various embodiments of an epicardial anchor device are described in more detail below with reference to specific embodiments.

Figure 2:
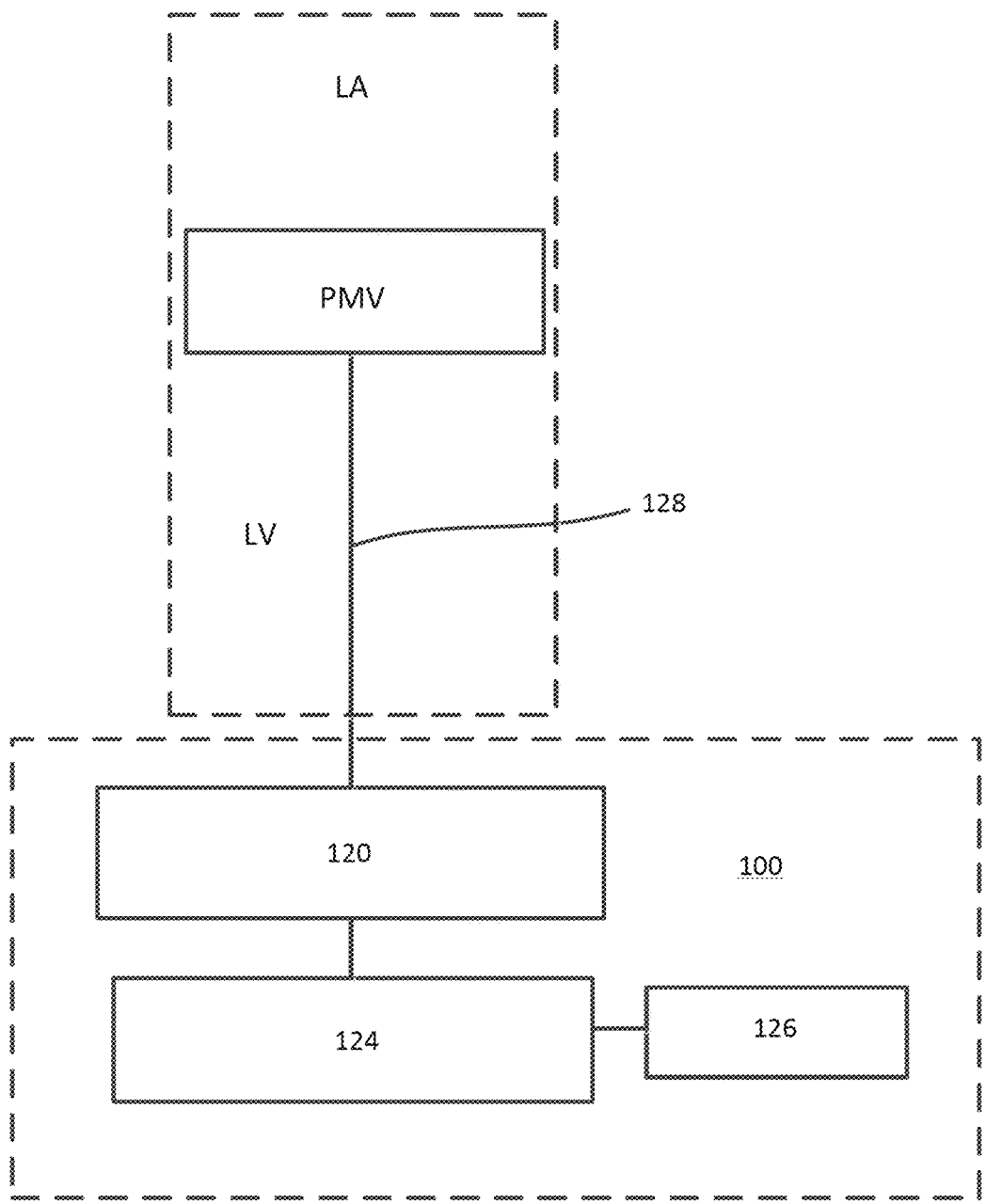
FIG. 2 is a schematic illustration of an epicardial anchor device, according to an embodiment.
Figure 3:
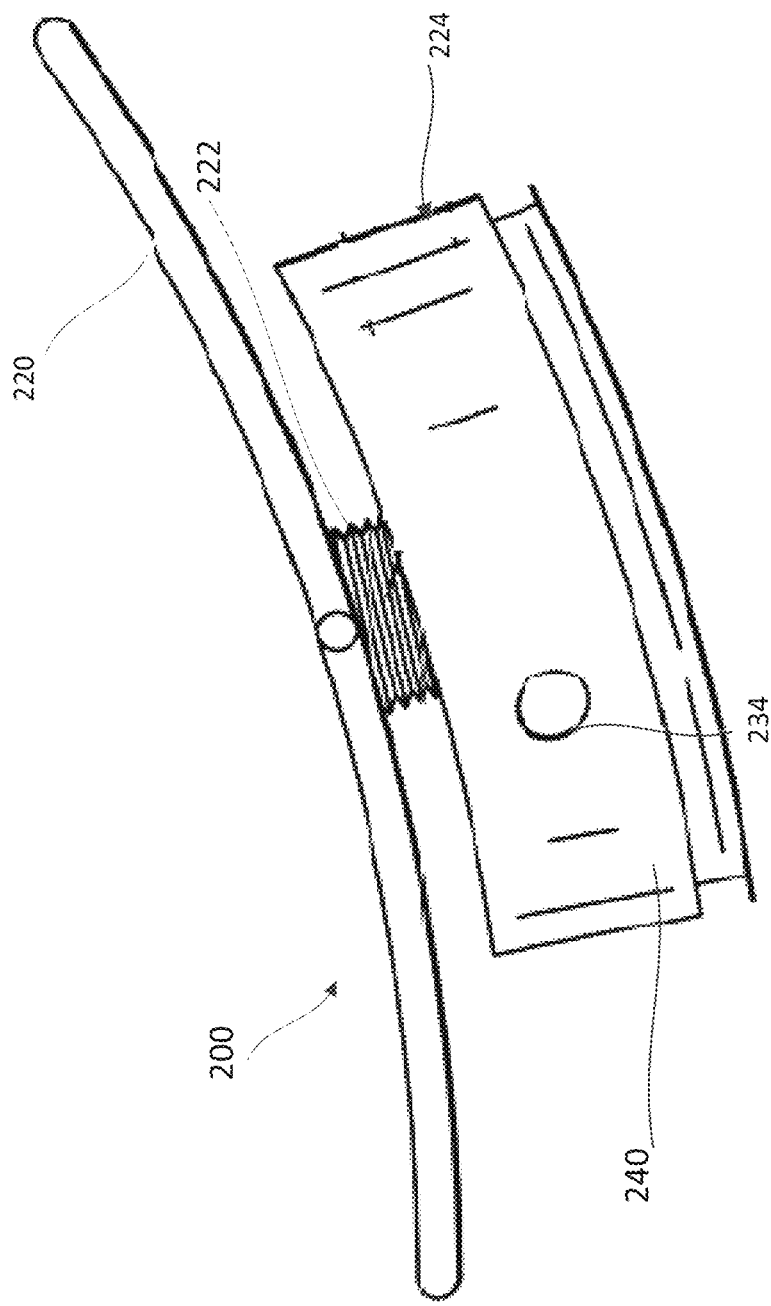
FIG. 3 is a side view of an epicardial anchor device, according to an embodiment.
Figure 4:
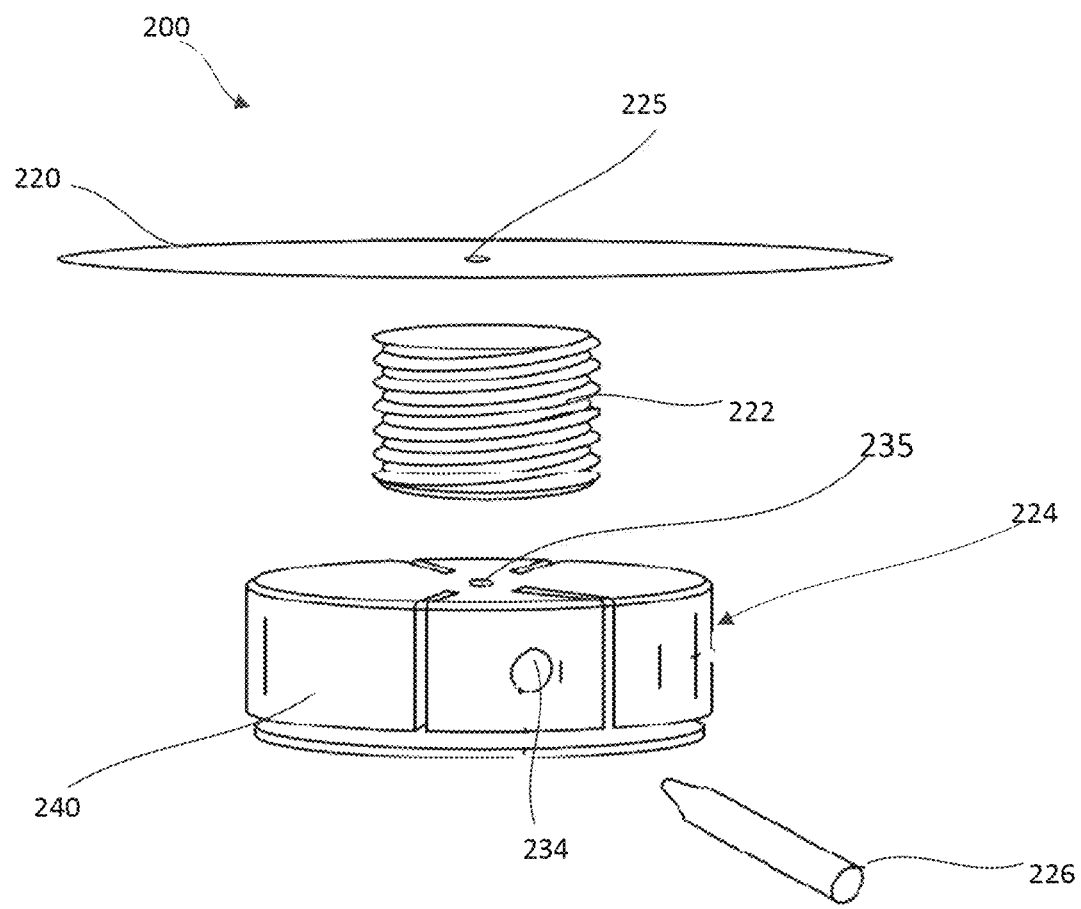
FIG. 4 is an exploded side view of the epicardial anchor device of FIG. 3.

FIG. 2 is a schematic illustration of an epicardial anchor device 100 (also referred to herein as "anchor device" or "epicardial anchor") according to an embodiment. The anchor device 100 can be used to anchor or secure a prosthetic mitral valve PMV deployed between the left atrium and left ventricle of a heart. The anchor device 100 can be used, for example, to anchor or secure the prosthetic mitral valve PMV via a suturing tether 128 as described above with respect to FIG. 1. The anchor device 100 can also seal a puncture formed in the ventricular wall (not shown in FIG. 2) of the heart during implantation of the prosthetic mitral valve PMV. The anchor device 100 can also be used in other applications to anchor a medical device (such as any prosthetic atrioventricular valve or other heart valve) and/or to seal an opening such as a puncture.

The anchor device 100 can include a pad (or pad assembly) 120, a tether attachment member 124 and a locking pin 126. In some embodiments, the anchor device 100 can include a sleeve gasket (not shown in FIG. 2) as described with respect to FIGS. 3-6. The pad 120 can contact the epicardial surface of the heart and can be constructed of any suitable biocompatible surgical material. The pad 120 can be used to assist the sealing of a surgical puncture formed when implanting a prosthetic mitral valve. In some embodiments, the pad 120 can include a slot that extends radially to an edge of the pad 120 such that the pad 120 can be attached to, or disposed about, the tether 128 by sliding the pad 120 onto the tether 128 via the slot. Such an embodiment is described below with respect to FIGS. 9 and 10.

In some embodiments, the pad 120 can be made with a double velour material to promote ingrowth of the pad 120 into the puncture site area. For example, pad or felt pledgets can be made of a felted polyester and may be cut to any suitable size or shape, such as those available from Bard® as PTFE Felt Pledgets having a nominal thickness of 2.87 mm. In some embodiments, the pad 120 can be larger in diameter than the tether attachment member 124. The pad 120 can have a circular or disk shape, or other suitable shapes.

The tether attachment member 124 can provide the anchoring and mounting platform to which one or more tethers 128 can be coupled (e.g., tied or pinned). The tether attachment member 124 can include a base member (not shown) that defines at least a portion of a tether passageway (not shown) through which the tether 128 can be received and pass through the tether attachment member 124, and a locking pin channel (not shown) through which the locking pin 126 can be received. The locking pin channel can be in fluid communication with the tether passageway such that when the locking pin 126 is disposed in the locking pin channel, the locking pin 126 can contact or pierce the tether 128 as it passes through the tether passageway as described in more detail below with reference to specific embodiments.

The locking pin 126 can be used to hold the tether 128 in place after the anchor device 100 has been tightened against the ventricular wall and the tether 128 has been pulled to a desired tension. For example, the tether 128 can extend through a hole in the pad 120, through a hole in a sleeve gasket (if the anchor device includes a sleeve gasket), and through the tether passageway of the tether attachment member 124. The locking pin 126 can be inserted or moved within the locking pin channel 134 such that it pierces or otherwise engages the tether 128 as the tether 128 extends through the tether passageway of the tether attachment member 124. Thus, the locking pin 126 can intersect the tether 128 and secure the tether 128 to the tether attachment member 124.

The tether attachment member 124 can be formed with, a variety of suitable biocompatible material. For example, in some embodiments, the tether attachment member 124 can be made of polyethylene, or other hard or semi-hard polymer, and can be covered with a polyester velour to promote ingrowth. In other embodiments, the tether attachment member 124 can be made of metal, such as, for example, Nitinol®, or ceramic materials. The tether attachment member 124 can be various sizes and/or shapes. For example, the tether attachment member 124 can be substantially disk shaped.

In some embodiments the tether attachment member 124 can include a lever arm (not shown in FIG. 2) that can be moved between an open position to load the tether 128 within the tether attachment member 124, and a closed position to secure the tether 128 to the tether attachment member 124. For example, in some embodiments, when the lever arm is moved to the closed position, the tether passageway is brought into an intersecting relation with the locking pin channel such that the locking pin 126 engages the tether 128 disposed within the tether passageway. In some embodiments, when the lever arm is in the open position, a tool can be used to move the locking pin within the locking pin channel such that the locking pin engages the tether 128 disposed within the tether passageway. In such an embodiment, after the locking pin 126 secures the tether 128, the lever arm can be moved to the closed position.

In some embodiments, the tether attachment member 124 can include a hub that is movably coupled to the base member of tether attachment member 124. The hub can define a channel that can receive a portion of the locking pin (or locking pin assembly) 126 such that as the hub is rotated, the hub acts as a cam to move the locking pin 126 linearly within the locking pin channel. As with previous embodiments, as the locking pin 126 is moved within the locking pin channel, the locking pin can engage or pierce the tether 128 disposed within the tether passageway and secure the tether 128 to the tether attachment member 124. Such an embodiment is described herein with respect to FIGS. 22-31.

In use, after a PMV has been placed within a heart, the tether extending from the PMV can be inserted into the tether passageway of the anchor device 100 and the tension on the tether attachment device can be adjusted to a desired tension. Alternatively, in some cases, the tether extending from the PMV can be coupled to the anchor device 100 prior to the PMV being placed within the heart. The anchor device 100 (e.g., some portion of the anchor device such as the tether attachment member 124, or the lever arm or hub depending on the particular embodiment) can be actuated such that the locking pin 126 intersects the tether passageway and engages a portion of the tether disposed within the tether passageway, securing the tether to the tether attachment member. In some embodiments, prior to inserting the tether into the tether passageway, the anchor device 100 can be actuated to configure the anchor device 100 to receive the tether. For example, if the tether attachment member includes a lever arm movably coupled to the base member, the lever arm may need to be moved to an open position to allow the tether to be inserted. In some embodiments, the anchor device 100 can be actuated by rotating a hub relative to a base member of the tether attachment member 124 such that the locking pin 126 is moved from a first position in which the locking pin is spaced from the tether passageway and a second position in which the locking pin intersects the tether passageway and engages or pierces the portion of the tether.

One implementation of the epicardial anchor device 100 is shown in FIGS. 3-6. An epicardial anchor device 200 (also referred to herein as "anchor device" or "epicardial anchor") can include a flexible pad 220, a sleeve gasket 222, a tether attachment member 224 and a locking pin 226 (shown in FIG. 4). The anchor device 200 can be used to anchor or secure a prosthetic mitral valve (not shown in FIGS. 3-6) via a suturing tether 228 shown in FIGS. 5 and 6. The anchor device 200 can also seal a puncture 230 formed in the ventricular wall V (see FIGS. 5 and 6) of the heart during implantation of the prosthetic mitral valve.

The flexible pad 220 (also referred to herein as "pad") can contact the epicardial surface of the heart and can be constructed of any suitable biocompatible surgical material. The pad 220 can be used to assist the sealing of a surgical puncture (e.g., puncture 230) formed when implanting a prosthetic mitral valve. The pad 220 can be made with the same or similar materials as described above for pad 120, and can be various sizes and shapes. The pad 220 is shown as having a circular or disk shape, however it should be understood that other suitable shapes can alternatively be used. The pad 220 defines a hole 225 (see FIGS. 4 and 6) through which the tether 228 (shown in FIGS. 5 and 6) can be received as described in more detail below.

The sleeve gasket 222 can be disposed between the pad 220 and the tether attachment member 224 and can be used to seal a gap or leakage that may occur between the pad 220 and the tether attachment member 224. The sleeve gasket 222 can be made of, for example, a flexible material such that it can be compressed when the tether attachment member 224 and/or pad 220 are tightened against the puncture site, e.g. against the ventricular wall. The sleeve gasket 222 may be a separate component coupled to the pad 220 and the tether attachment member 224 or can be formed integrally or monolithically with the pad 220 and/or the tether attachment member 224. The sleeve gasket 222 can be used to prevent hemodynamic leakage that may flow along the path of the suturing tether 228. The sleeve gasket 222 can also define a hole (not shown) through which the tether 228 can be received.

The tether attachment member 224 can provide the anchoring and mounting platform to which one or more tethers 228 (see FIGS. 5 and 6) may be coupled (e.g., tied). The tether attachment member 224 includes a base member 240 that defines an axial tether passageway 235 through which the tether 228 can be received and pass through the tether attachment member 224, and a locking pin channel 234 through which the locking pin 226 can be received. The locking pin channel 234 can be in fluid communication with the tether passageway 235 such that when the locking pin 226 is disposed in the locking pin channel 234, the locking pin 226 can contact the tether 228 as it passes through the tether passageway 235 as described in more detail below. The locking pin 226 can be used to hold the tether 228 in place after the anchor device 200 has been tightened against the ventricular wall V. For example, the tether 228 can extend through the hole 225 of the pad 220, through the hole (not shown) of the sleeve gasket 222, and through the tether passageway 235 of the tether attachment member 224. The locking pin 226 can be inserted through the locking pin channel 234 such that it pierces the tether 228 as the tether 228 extends through the tether passageway 235 of the tether attachment member 224. Thus, the locking pin 226 can laterally intersect the tether 228 and secure the tether 228 to the tether attachment member 224.

The tether attachment member 224 can be made of any suitable biocompatible material. For example, in some embodiments, the tether attachment member 224 can be made of polyethylene, or other hard or semi-hard polymer, and can be covered with a polyester velour to promote ingrowth. In other embodiments, the tether attachment member 224 can be made of metal, such as, for example, Nitinol®, or ceramic materials. The tether attachment member 224 can be various sizes and/or shapes. For example, the tether attachment member 224 can be substantially disk shaped.

In some embodiments, the tether attachment member 224 can be substantially disk shaped and have a diameter between, for example, 1.0-3.0 cm. In other embodiments, the tether attachment member 224 can have a diameter, for example, between 0.2-5.0 cm. For example, a larger size tether attachment member 224 may be desirable to use in, for example, a hernia repair, gastrointestinal repairs, etc.

The disk shape of the tether attachment member 224 used to capture and anchor a suture can also be used with little or no trauma to the tissue at the site of the anchor, unlike suture anchors that bore into tissue with screws or barbs. Further, the disk shaped tether attachment member 224 can be easily and quickly slid over the tether 228, instead of using stitches, which can allow for the effective permanent closure of large punctures. Surgically closing large punctures by sewing can be time consuming and difficult. When closing a puncture in the heart, adding the difficulty of requiring a surgeon to sew the puncture closed can increase the likelihood of life threatening complications to the patient. This is especially so in a situation where a prosthetic heart valve is delivered and deployed without opening the chest cavity using transcatheter technologies. Sewing a ventricular puncture closed in this situation may be undesirable.

Figure 5:
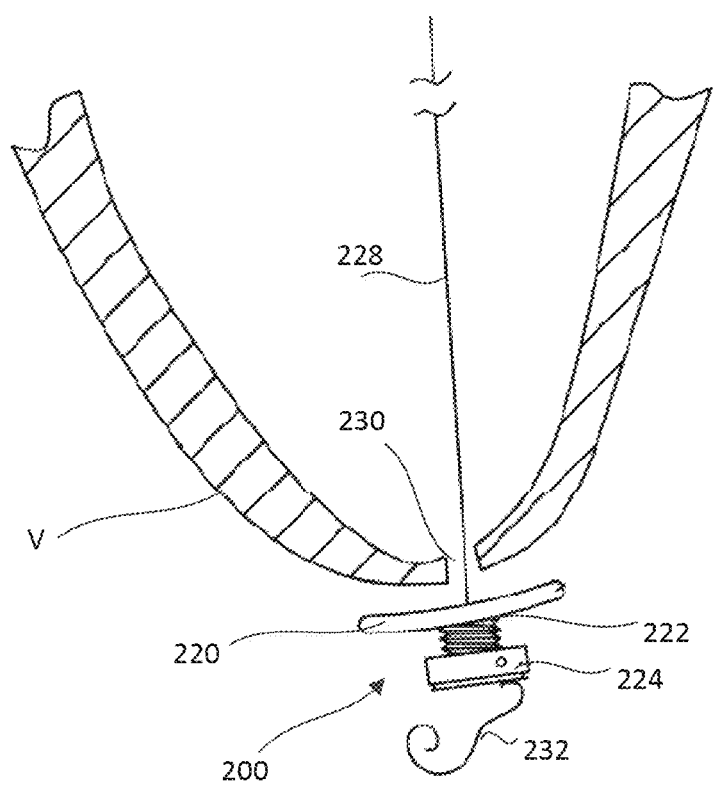
FIG. 5 is a side view of the epicardial anchor device of FIG. 3 shown disposed at a spaced distance from a puncture site in an epicardial surface of a ventricular wall and showing a sleeve gasket of the epicardial anchoring device in an uncompressed state or configuration.
Figure 6:
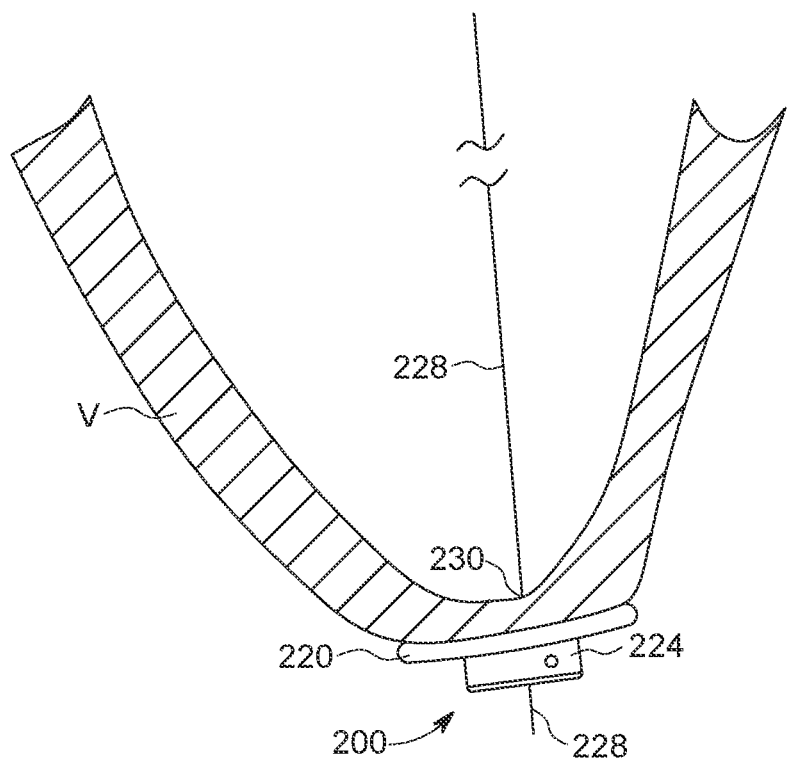
FIG. 6 is a side view of the epicardial anchor device and ventricular wall of FIG. 5, shown with the anchoring device compressed against the puncture site and ventricular wall and the gasket in a compressed state or configuration.

FIGS. 5 and 6 illustrate the tether 228 extending through the puncture site 230 within a left ventricular wall V of a heart and coupled to the anchor device 200. FIG. 5 illustrates the anchor device 200 prior to being tightened against the epicardial surface of the ventricular wall V, and the sleeve gasket 222 in an uncompressed state or configuration. The tether 228 can optionally be wound around the tether attachment member 224 to further improve anchoring.

FIG. 6 illustrates the anchor device 200 tightened against the epicardial surface of the ventricular wall V. As shown in FIG. 6, the anchor device 200 can be compressed against the puncture site 230 and contact the epicardial surface. An end portion 232 (shown in FIG. 5) of the tether 228 can be trimmed after the tether 228 has been secured to the tether attachment member 224 or after the anchor device 200 has been secured against the epicardial surface.

Figure 7:
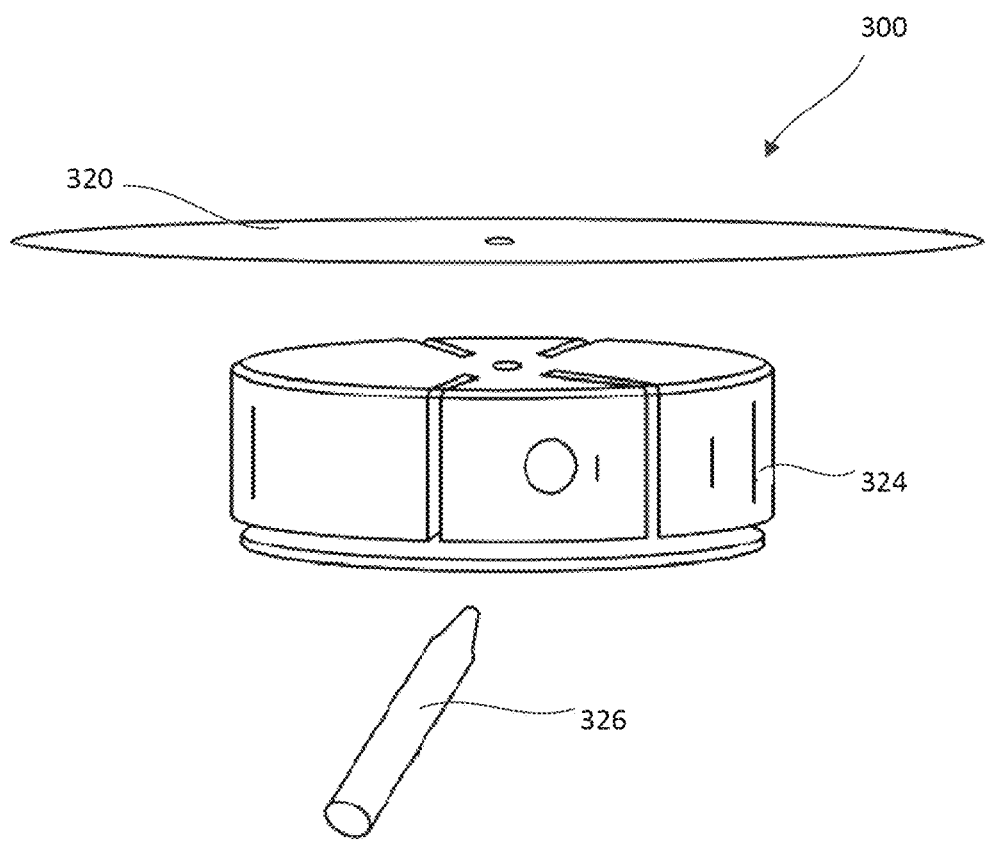
FIG. 7 is an exploded side view of an epicardial anchor device, according to another embodiment.

FIG. 7 illustrates an embodiment of an epicardial anchor device 300 (also referred to herein as "anchor device" or "epicardial anchor") that is similar to the anchor device 200 except the anchor device 300 does not include a sleeve gasket (e.g., sleeve gasket 222 described above). The anchor device 300 can include a flexible pad 320, a tether attachment member 324 and a locking pin 326, which can be configured the same as or similar to the flexible pad 220, the tether attachment member 224 and the locking pin 226, respectively, described above. The anchor device 300 can be used the same as or similar to anchor device 200 to secure a prosthetic mitral valve (not shown) via a suturing tether (not shown). The anchor device 300 may be desirable to use, for example, when an anti-leakage sleeve is unnecessary to prevent hemodynamic leakage that may flow along the path of the suturing tether.

Figure 8:
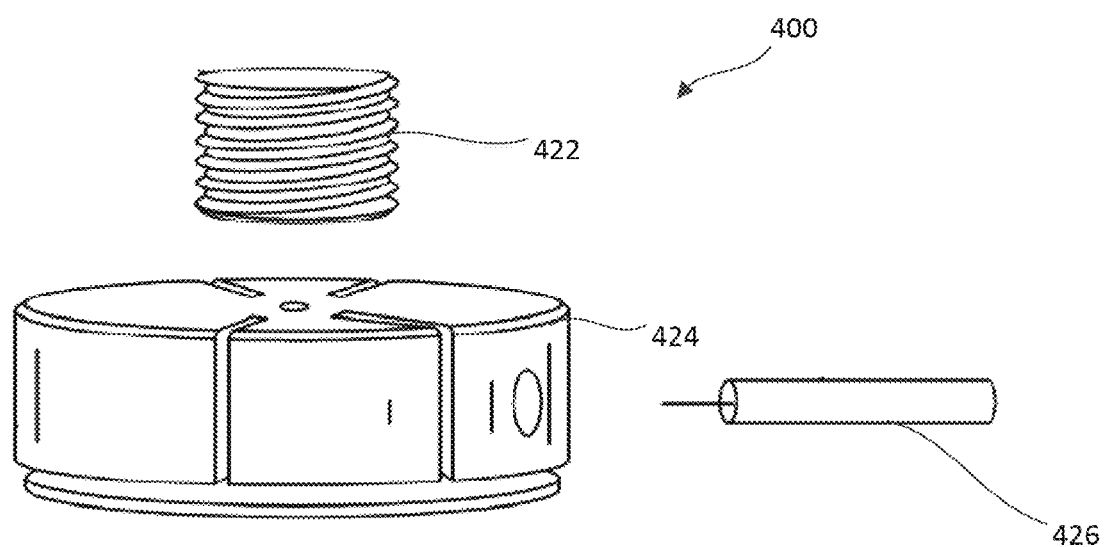
FIG. 8 is an exploded side view of an epicardial anchor device, according to another embodiment.

FIG. 8 illustrates an embodiment of an epicardial anchor device 400 (also referred to herein as "anchor device" or "epicardial anchor") that is similar to the anchor device 200 and the anchor device 300 except the anchor device 400 does not include a pad (e.g., pads 220 and 320). The anchor device 400 can include a tether attachment member 424, a sleeve gasket 422 and a locking pin 426, which can be configured the same as or similar to the tether attachment member 224, the sleeve gasket 222 and the locking pin 226, respectively, described above. The anchor device 400 can be used to anchor or secure a prosthetic mitral valve (not shown) via a tether (not shown) in the same or similar manner as described above for previous embodiments. The anchor device 400 may be desirable to use, for example, when a flexible pad is unnecessary, for example, when the tether is moved to a new location. In such a case, the ventricular puncture would be small (e.g., a small diameter) and may not require the pad for bleeding control.

Figure 9:
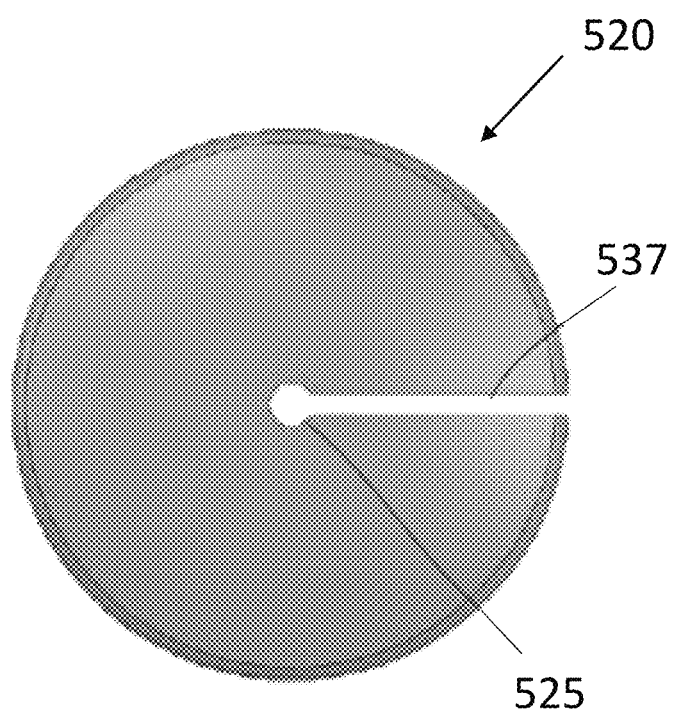
FIG. 9 is a top view of a flexible pad that can be included in an epicardial anchor device, according to an embodiment.
Figure 10:
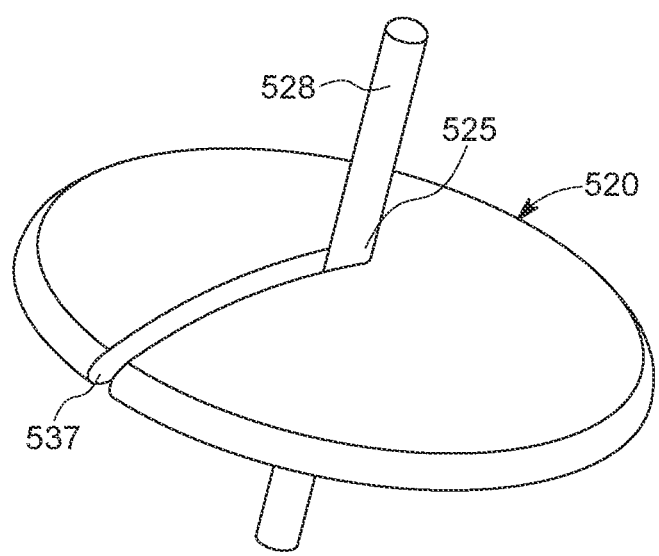
FIG. 10 is a perspective view of the flexible pad of FIG. 9 and a portion of a tether disposed therethrough.

FIGS. 9 and 10 illustrate an embodiment of a pad 520 that can be included in an epicardial anchor device as described herein. The pad 520 defines an axial hole 525 and a slot 537 that communicates with hole 525. The slot 537 extends radially to an outer edge of the pad 520 such that the pad 520 can be disposed about or removed from a tether 528 (see FIG. 10) without sliding the pad 520 down the length of tether 528. For example, the pad 520 can be disposed about the tether 528 by laterally sliding the pad 520 from the side such that the tether is inserted into the slot 537 and positioned within the opening 525 of the pad 520. The pad 520 can be secured to the tether with, for example, pins, clamps, etc.

To remove the pad 520, the pad 520 can similarly slide off from the side, for example, outside of the apex of the ventricle of the heart. Thus, the pad 520 can be removed without removing the entire anchor device. The pad 520 can be formed with the same or similar materials as described above for previous embodiments (e.g., pad 220, 320, 420), and can be used to close a puncture site (e.g., in a ventricular wall) as described above.

The pad 520 can also enable the use of an introducer sheath at the apex, which would limit the amount of motion and passes through the apex. For example, when the sheath is pulled back, a slotted pad 520 can be slid in from the side allowing control of the tether tension during sheath removal. The pad 520 with slot 537 can also be used independent of a sheath as described above.

Figure 11:
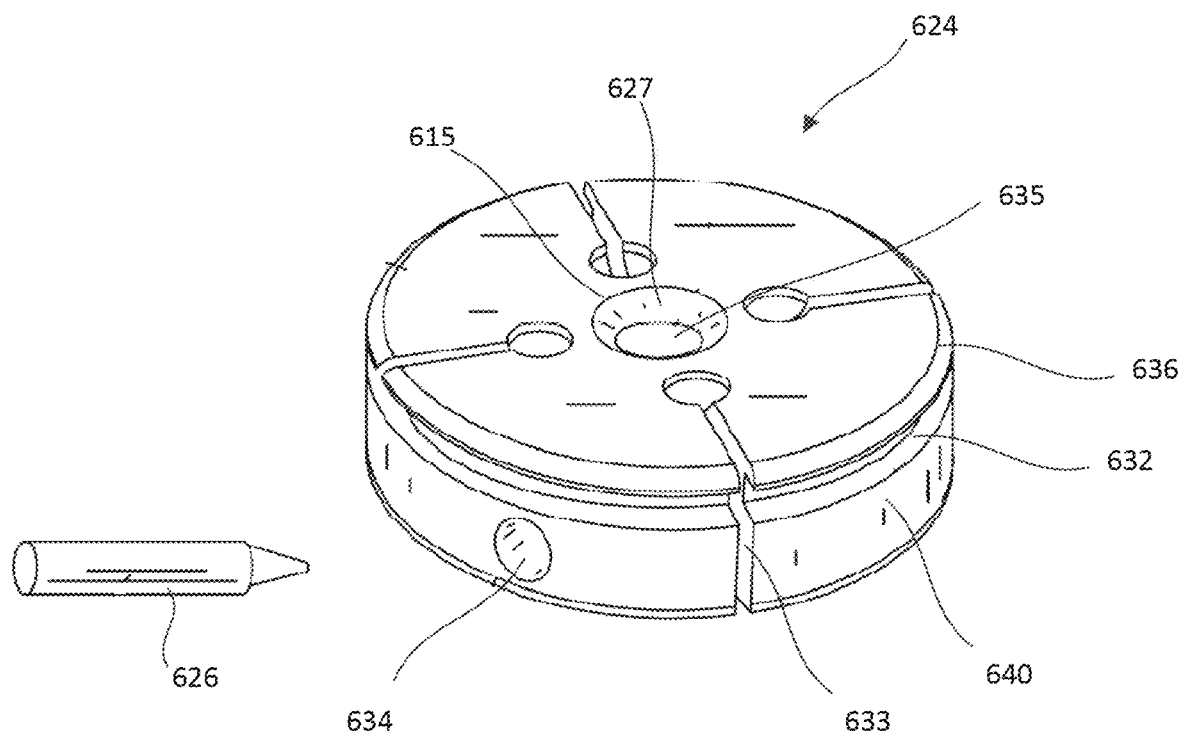
FIG. 11 is a perspective view of a locking pin and a tether attachment member, according to an embodiment.
Figure 12:
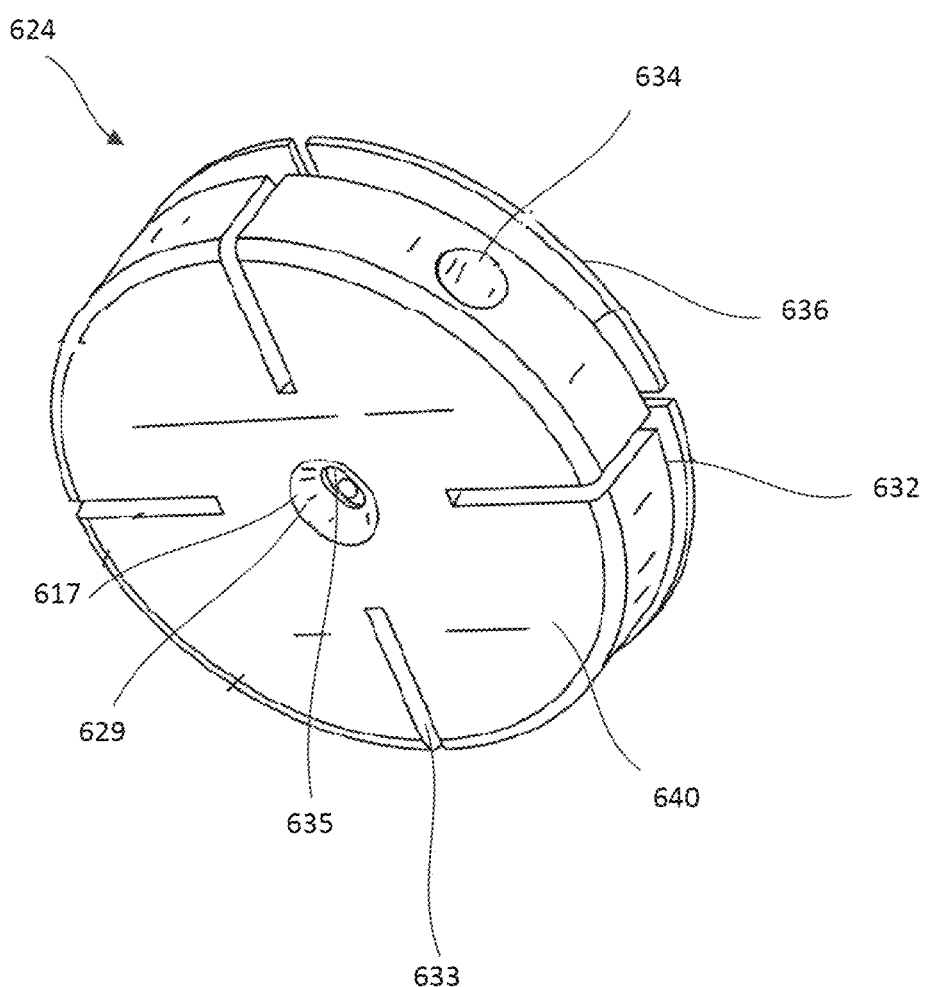
FIG. 12 is a bottom perspective view of the tether attachment member of FIG. 11.

FIGS. 11 and 12 illustrate an embodiment of a tether attachment member 624 that can be included within an anchor device as described herein. Various features described herein for tether attachment member 624 can also be included in the tether attachment members described herein for other embodiments (e.g., 124, 224, 324, 424). As described above, a locking pin 626 (shown in FIG. 11) can be used to secure a tether/suture to the tether attachment member 624 in a similar manner as described above for previous embodiments.

The tether attachment member 624 is shown having a disk shape and can include a base member 640 that defines a winding channel 632, an axial tether passageway 635, radial channels 633, and a locking pin channel 634 through which the locking pin 626 can be received. The base member 640 also defines a proximal opening 615 and a distal opening 617 each communicating with the tether passageway 835. The base member 640 can include a chamfered edge or lead-in portion 627 at the proximal opening 615, and a chamfered edge or lead-in portion 629 at the distal opening 617 to allow a suture (e.g., tether) to be easily threaded into the tether passageway 635 and reduce lateral cutting force of the tether attachment member 624 against the suture. The radial channels 633 can allow a user to quickly capture and seat a tether (not shown) that is intended to be anchored. The winding channel 632 can allow a user to quickly wind tether(s) around tether attachment member 624. The use of winding channel 632 with radial channel(s) 633 can allow a user to quickly anchor the tether while permitting the user to unwind and recalibrate the anchor device to adjust the tension on the tether (not shown) as appropriate for a particular use.

FIGS. 13-16 illustrate a portion of another embodiment of an epicardial anchor device 700. The epicardial anchor device 700 includes a tether attachment member 724 and a flexible pad or fabric member (not shown in FIGS. 13-16). The tether attachment member 724 includes a base member 740 that defines a locking pin channel 734 that can receive therein a locking pin 726 in a similar manner as described above for previous embodiments and a circumferential pad channel 742. The pad channel 742 can be used to secure the flexible pad or fabric member (not shown in FIGS. 13-16) of the epicardial anchor device 700 to the tether attachment member 724. For example, the flexible pad can be disposed on a distal end portion of the tether attachment member 724 such that when the anchor device 700 is secured to a ventricular wall as described above for previous embodiments, the flexible pad contacts the ventricular wall.

The tether attachment member 724 also defines tether passageway 735 through which a tether 728 (see, e.g., FIGS. 15 and 16) can be received, and a proximal opening 715 and a distal opening 717 each in communication with the tether passageway 735. A chamfered edge or lead-in portion 729 is included at or near the distal opening 717 to allow a tether 728 (see e.g., FIGS. 15 and 16) to be easily threaded into the tether passageway 735 and reduce lateral cutting force of the tether attachment member 724 against the tether 728.

Figure 13:
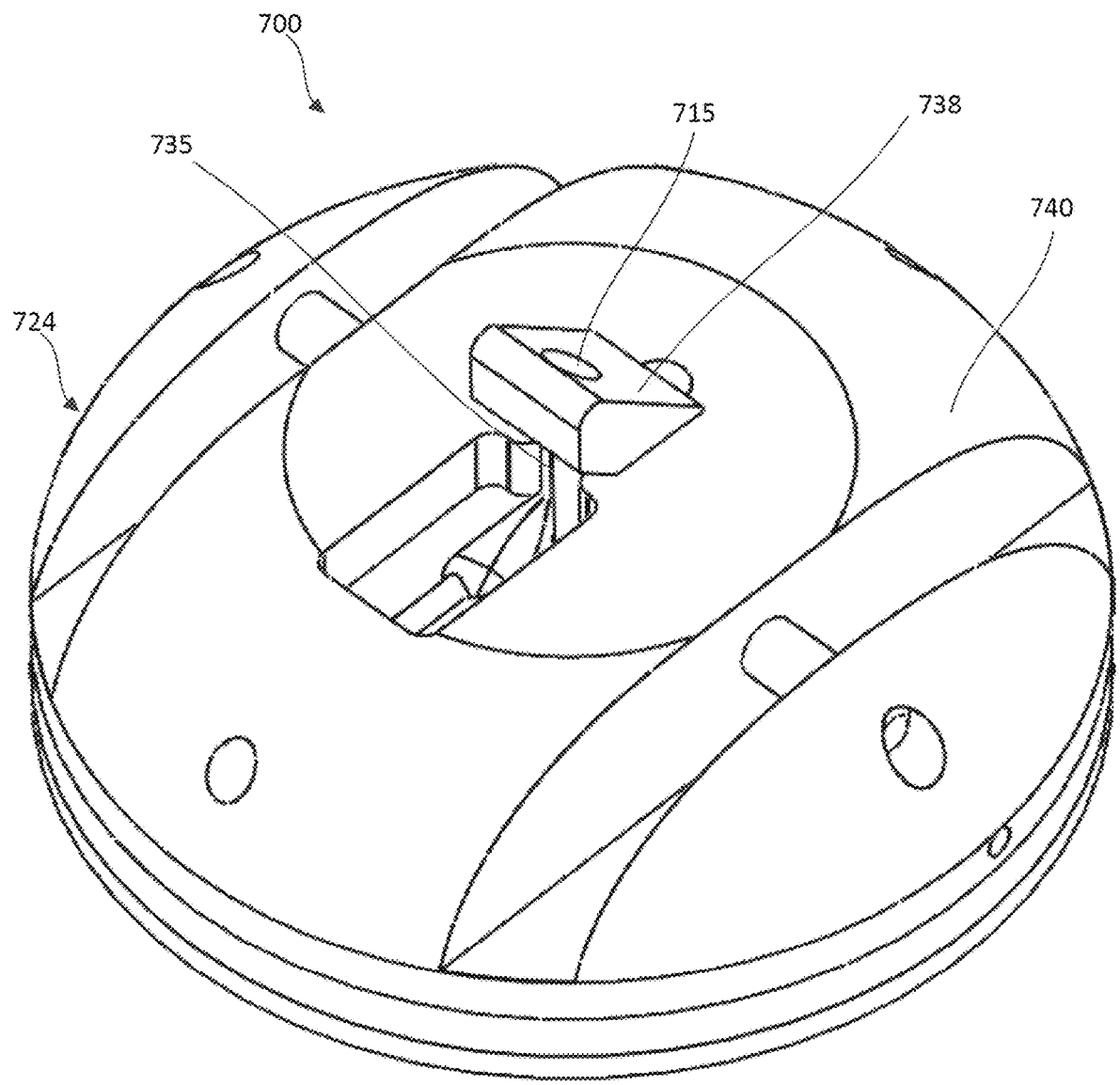
FIG. 13 is a top perspective view of a tether attachment member that can be used within an anchor device, according to an embodiment, with a lever arm shown in a first position.
Figure 14:
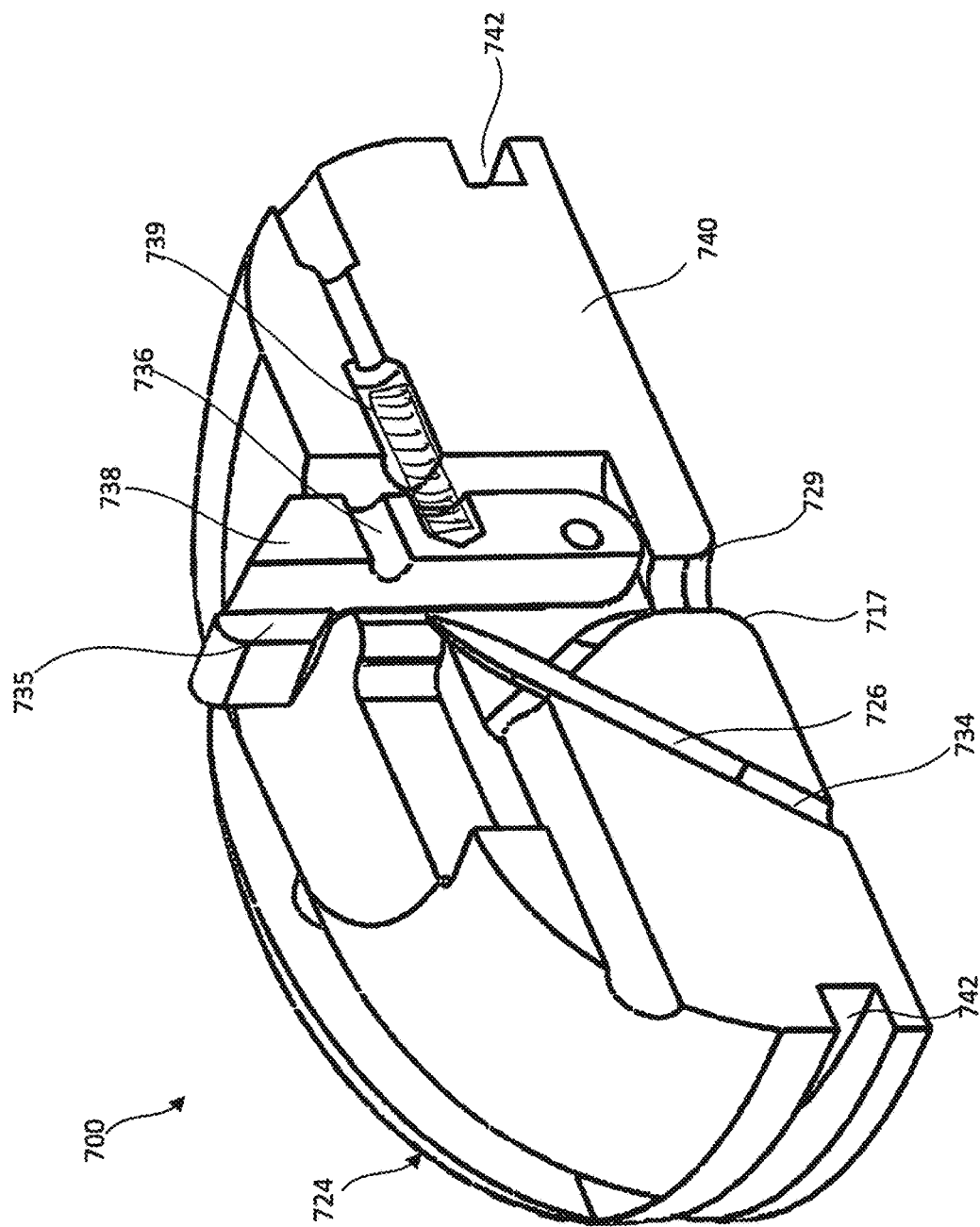
FIG. 14 is a cross-sectional perspective view of the tether attachment member of FIG. 13 with the lever arm shown in the first position.
Figure 15:
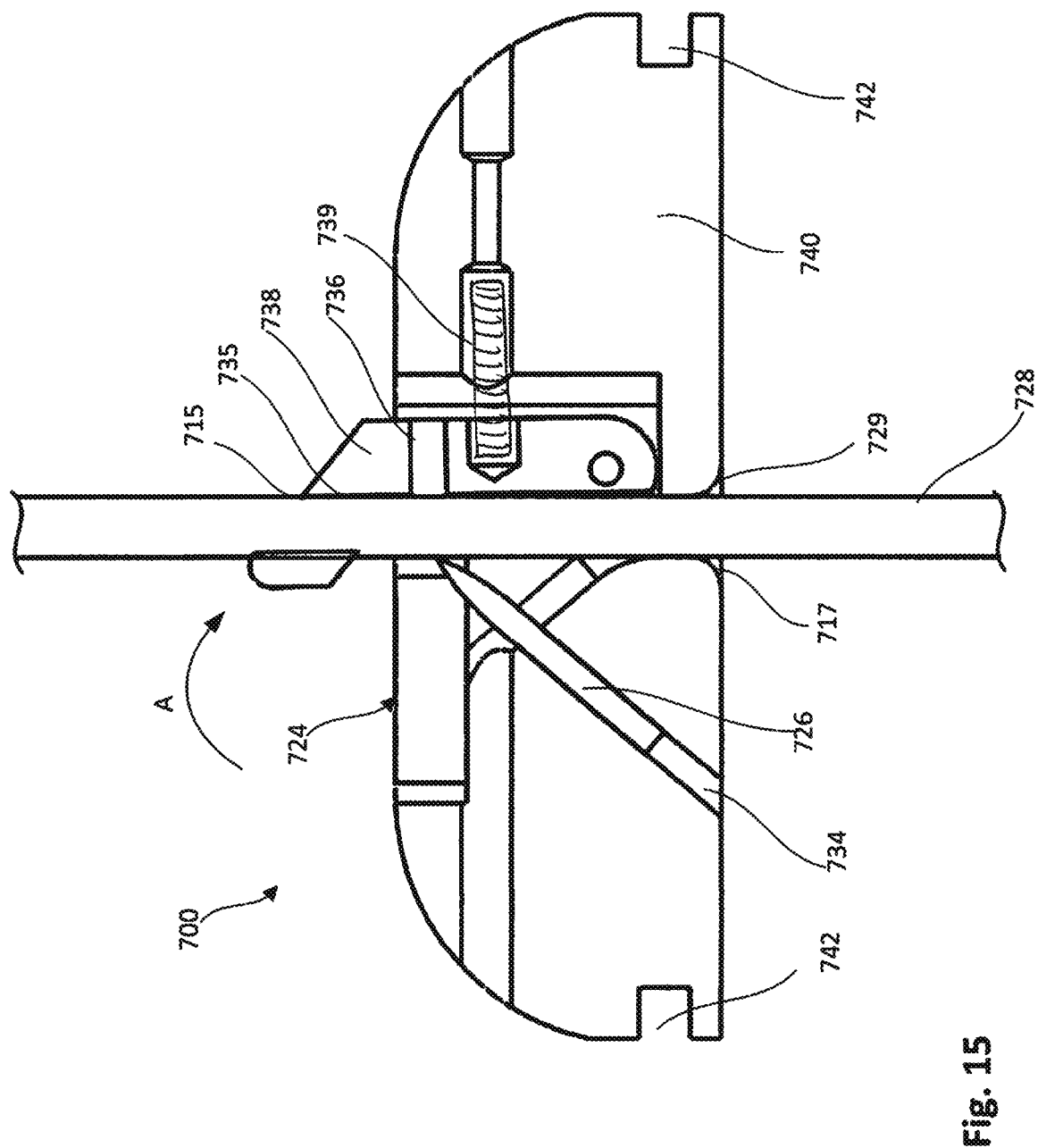
FIG. 15 is a cross-sectional side view of the tether attachment member of FIG. 13 with the lever arm shown in the first position and a portion of a tether extending through the device.
Figure 16:
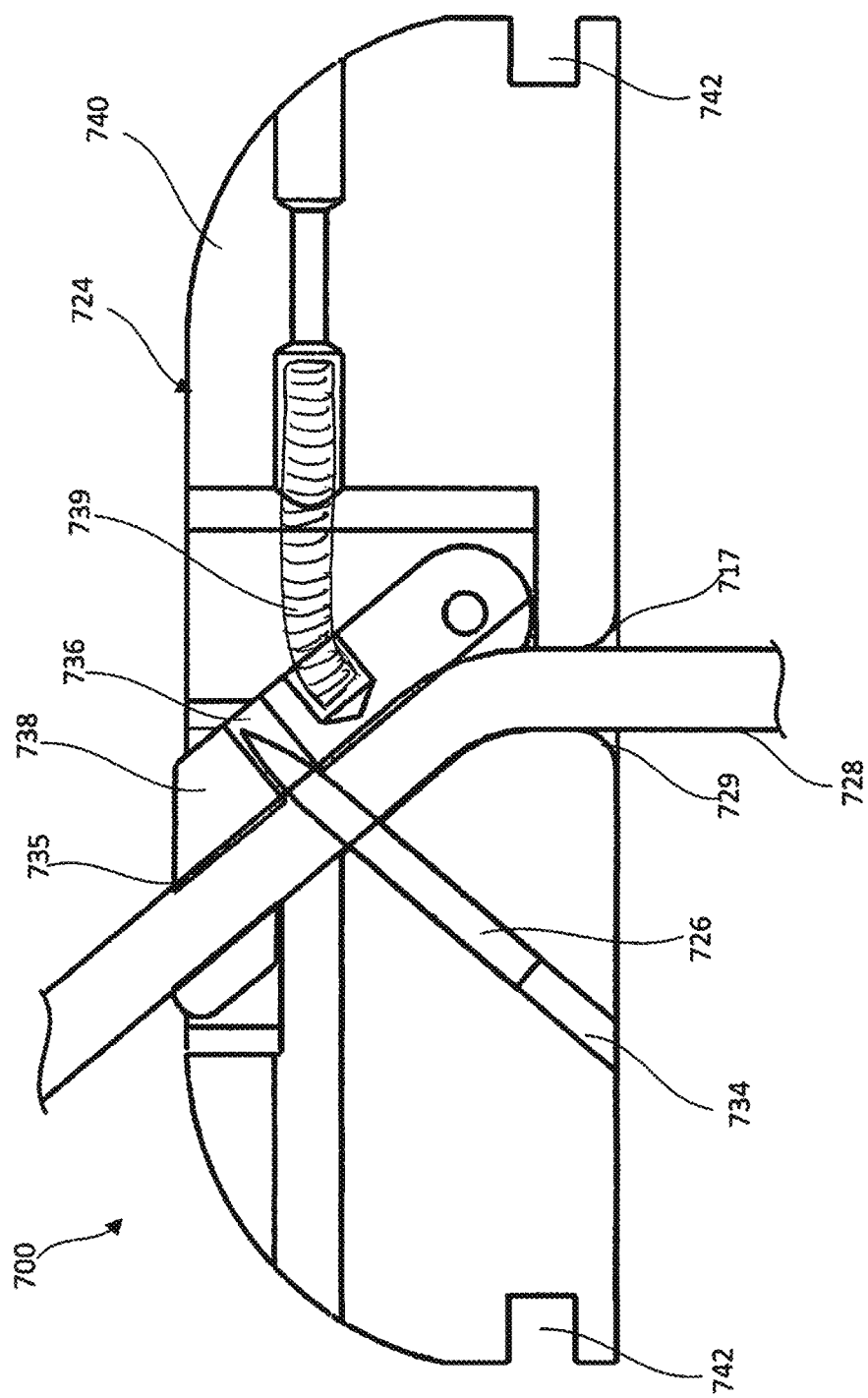
FIG. 16 is a cross-sectional side view of the tether attachment member of FIG. 13 with the lever arm shown in a second position and a portion of a tether extending through the device.

A lever arm 738 is coupled to the base member 740 that collectively with the base member 740 defines a tether passageway 735. The lever arm 738 can be moved between a first position, as shown in FIG. 16, in which the lever arm 738 is biased by a spring member 739 into a down position, and a second position, as shown in FIGS. 13-15, in which the lever arm 738 is placed in an extended position to allow the tether 728 to be placed within the tether passageway 735. For example, the lever arm 738 can be rotated in the direction of arrow A shown in FIG. 15 to move the lever arm 738 to its second or extended position. In some cases, a suture or cord can be used to pull the lever arm 738 to the extended second position.

When in the first position, as shown, for example, in FIGS. 14 and 15, a tip of the locking pin 726 is disposed at a spaced distance from the lever arm 738 and the tether passageway 735. When the locking pin 726 is spaced from the tether passageway 735, the tether 728 can be inserted into the tether passageway 735 as shown in FIG. 15. The tether 728 can then be tightened to a desired tension and the lever arm can then be released such that it is biased back to the first position, as shown in FIG. 16. When the lever arm 738 is moved (e.g., biased) to the first position, and with the tether 728 extending through the tether passageway 735, the locking pin 726 pierces or intersects with the tether 728 and the tip of the locking pin is then disposed within a cavity 736 defined by the lever arm 738 securing the tether 728 to the tether attachment member 724.

FIGS. 17-21 illustrate a portion of another embodiment of an epicardial anchor device 800 that includes a tether attachment member 824 and a flexible pad or fabric member (not shown in FIGS. 17-21). The tether attachment member 824 includes a base member 840 and a lever arm 838 pivotally coupled to the base member 840. The base member 840 defines a circumferential pad channel 842 in which the flexible pad can be coupled to the tether attachment member 824. For example, the flexible pad can be disposed on a distal end portion of the tether attachment member 824 such that when the anchor device 800 is secured to a ventricular wall as described above for previous embodiments, the flexible pad contacts the ventricular wall.

Figure 17:
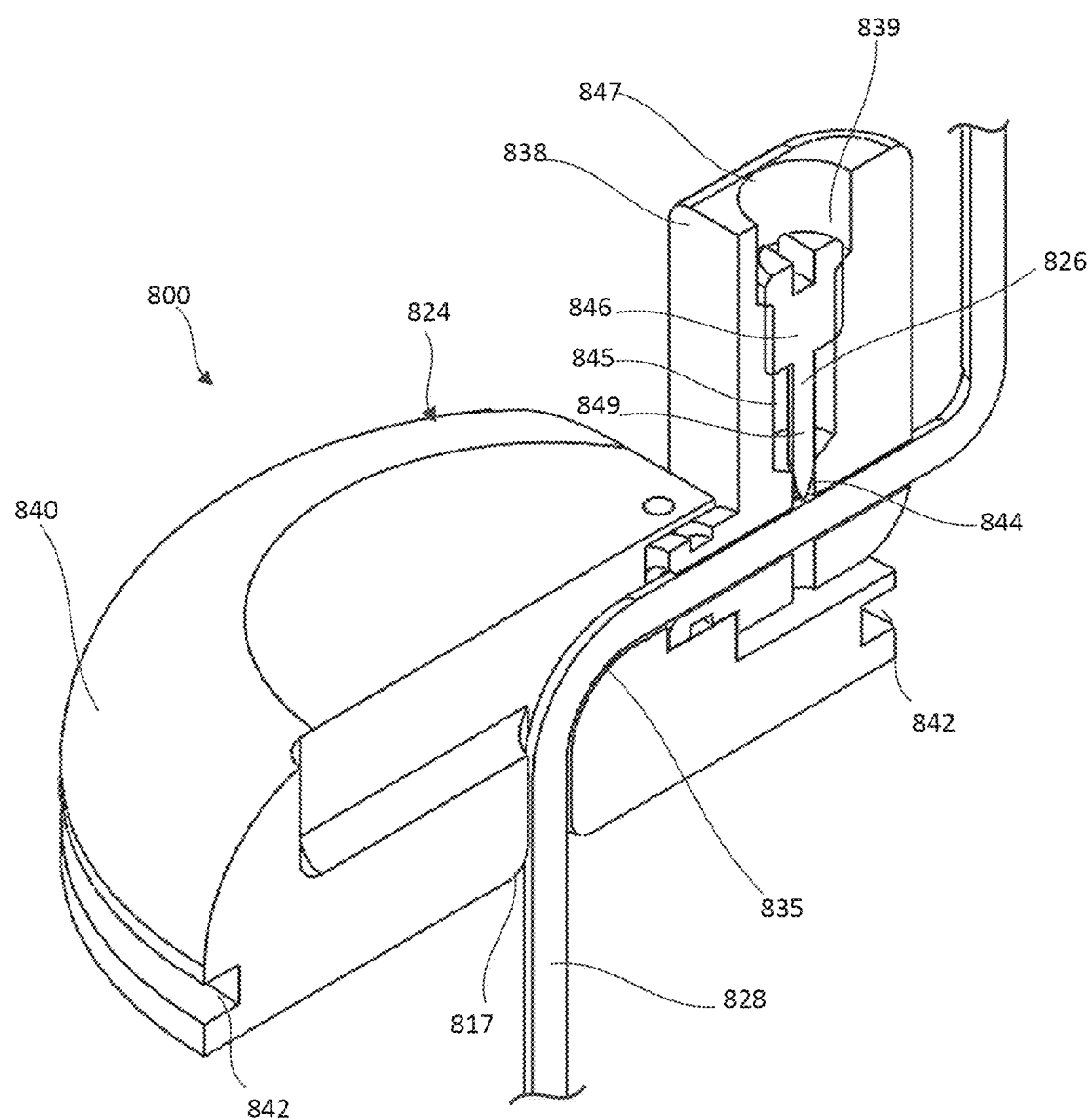
FIG. 17 is a cross-sectional perspective view of a tether attachment member, according to an embodiment, with an access arm of the anchor device shown in a first position and a portion of a tether extending through the device.

The lever arm 838 and the base member 840 collectively define a tether passageway 835 through which a tether 828 can be received, as shown in FIG. 17. The base member 840 also defines a distal opening 817 and an opening 815 each in fluid communication with the tether passageway 835. The tether 828 can be inserted through the distal opening 817 (the side to be implanted closest to the ventricular wall) and extend through a portion of the tether passageway 835 defined by the base member 840, and through a portion of the tether passageway 835 defined by the lever arm 838, and exit the opening 815. As with previous embodiments, the base member 840 includes a chamfered edge or lead-in portion 829 at the distal opening 817 of the tether passageway 835 to allow the tether 828 to be easily threaded into the tether passageway 835 and reduce lateral cutting force of the tether attachment member 824 against the tether 828.

Figure 18:
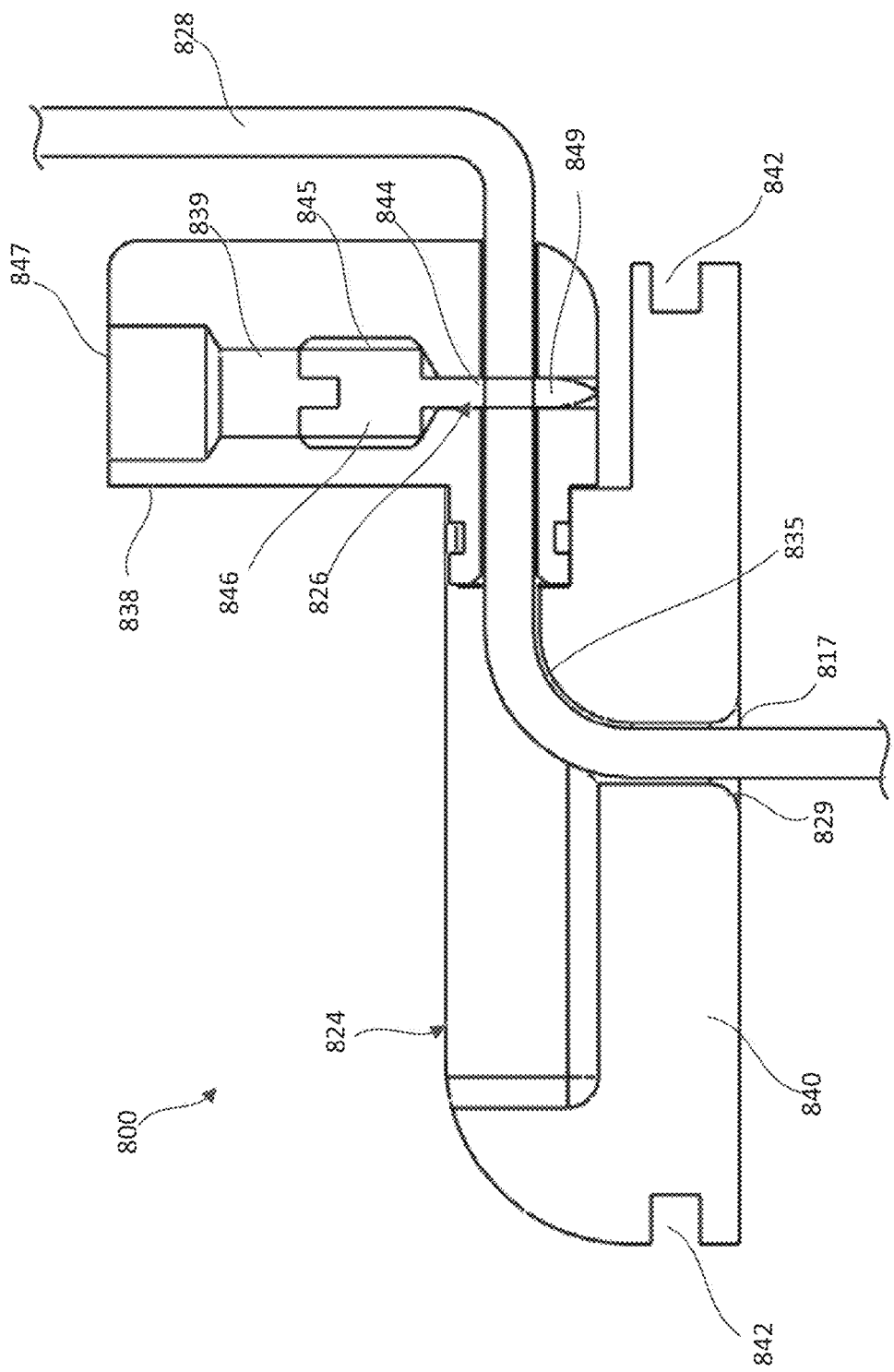
FIG. 18 is a side-cross-sectional view of the tether attachment member of FIG. 17 shown with the access arm in the first position and the portion of a tether extending through the device.

The lever arm 838 defines a locking pin channel 844 in which a locking pin 826 can be movably disposed. The locking pin 826 includes a driver portion 846 and a piercing portion 849. As shown in FIGS. 17 and 18, the locking pin channel 844 includes portions with varying diameters in which the driver portion 846 of the locking pin 826 can be movably disposed. For example, the driver portion 846 can be threadably coupled to the inner walls of the locking pin channel 844 such that the locking pin 826 can be moved between a first position, shown in FIG. 17, in which the driver portion 846 is disposed within a portion 839 of the locking pin channel 844 and the piercing portion 849 is spaced from the tether passageway 835, and a second position in which the driver portion 846 is disposed within a portion 845 (shown in FIGS. 17 and 18) of the locking pin channel 834, and the piercing portion 849 extends through the tether passageway 835, engaging or piercing the tether 828. The lever arm 838 also defines an opening 847 that communicates with the locking pin channel 844 and can receive a driving tool that can be used to move the locking pin 826 within the locking pin channel 844 as described in more detail below.

Figure 19:
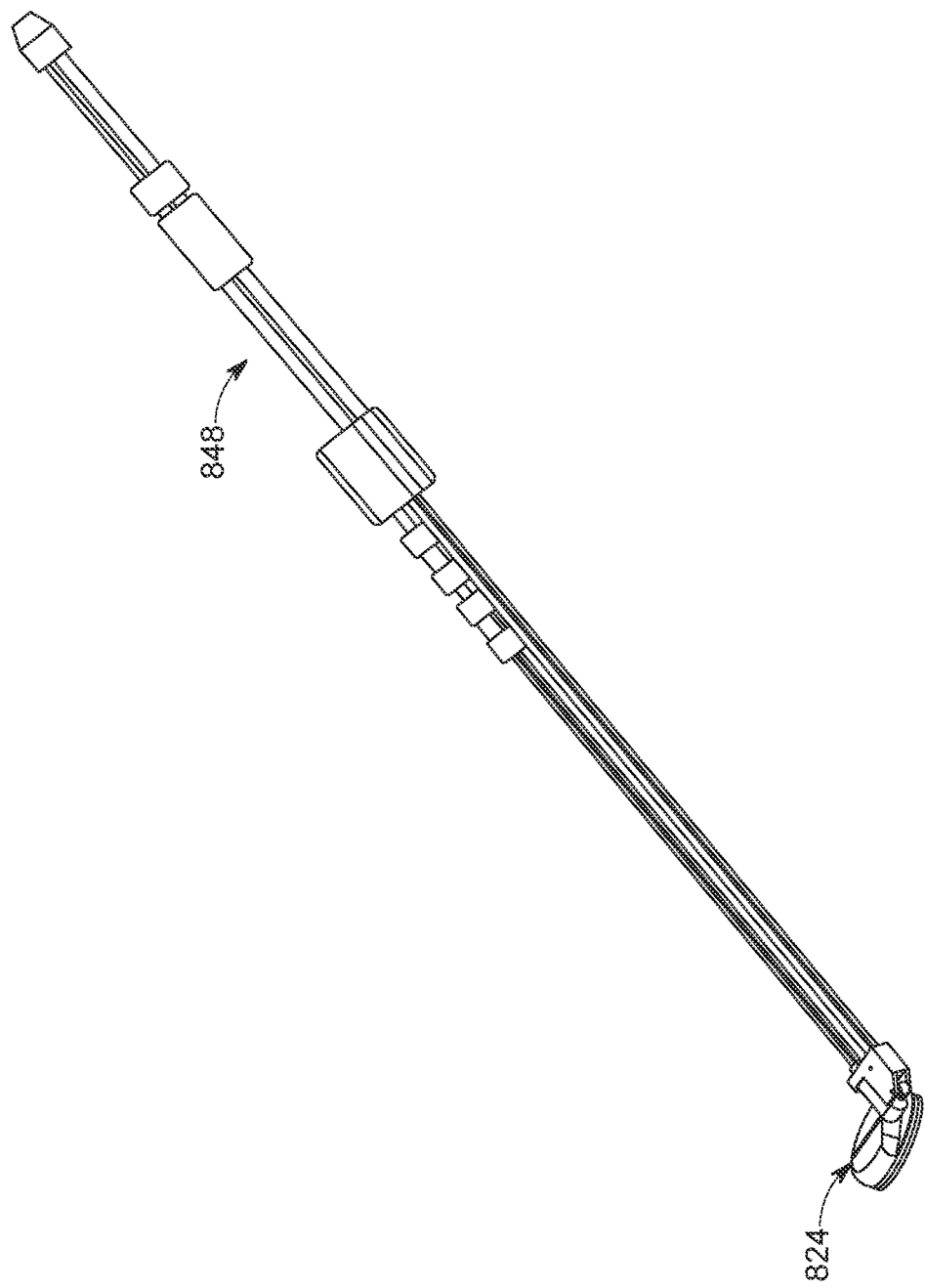
FIG. 19 is a perspective view of the tether attachment member of FIG. 17 with a delivery device coupled thereto.
Figure 20:
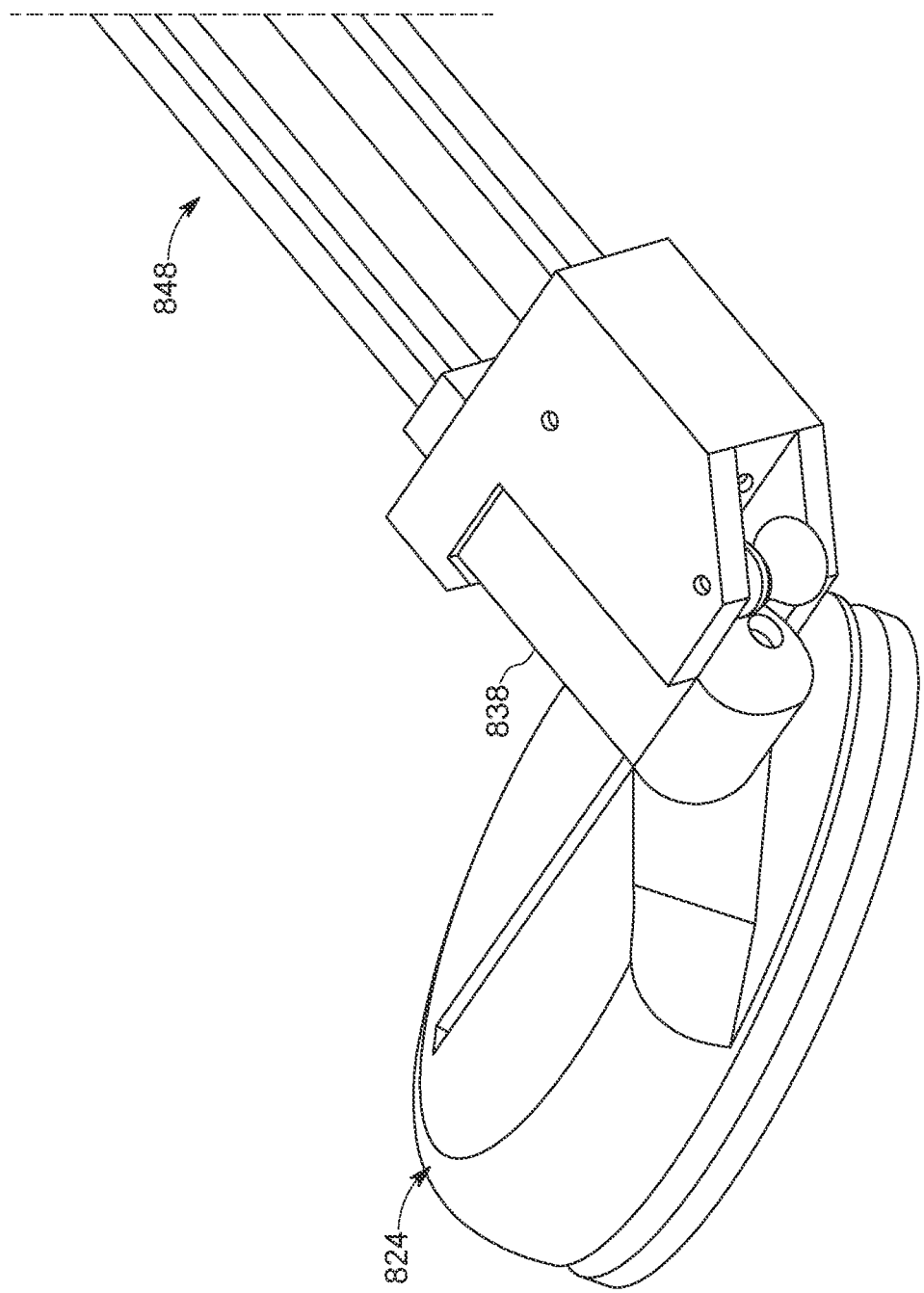
FIG. 20 is an enlarged view of the tether attachment member and a portion of the delivery device of FIG. 19.
Figure 21:
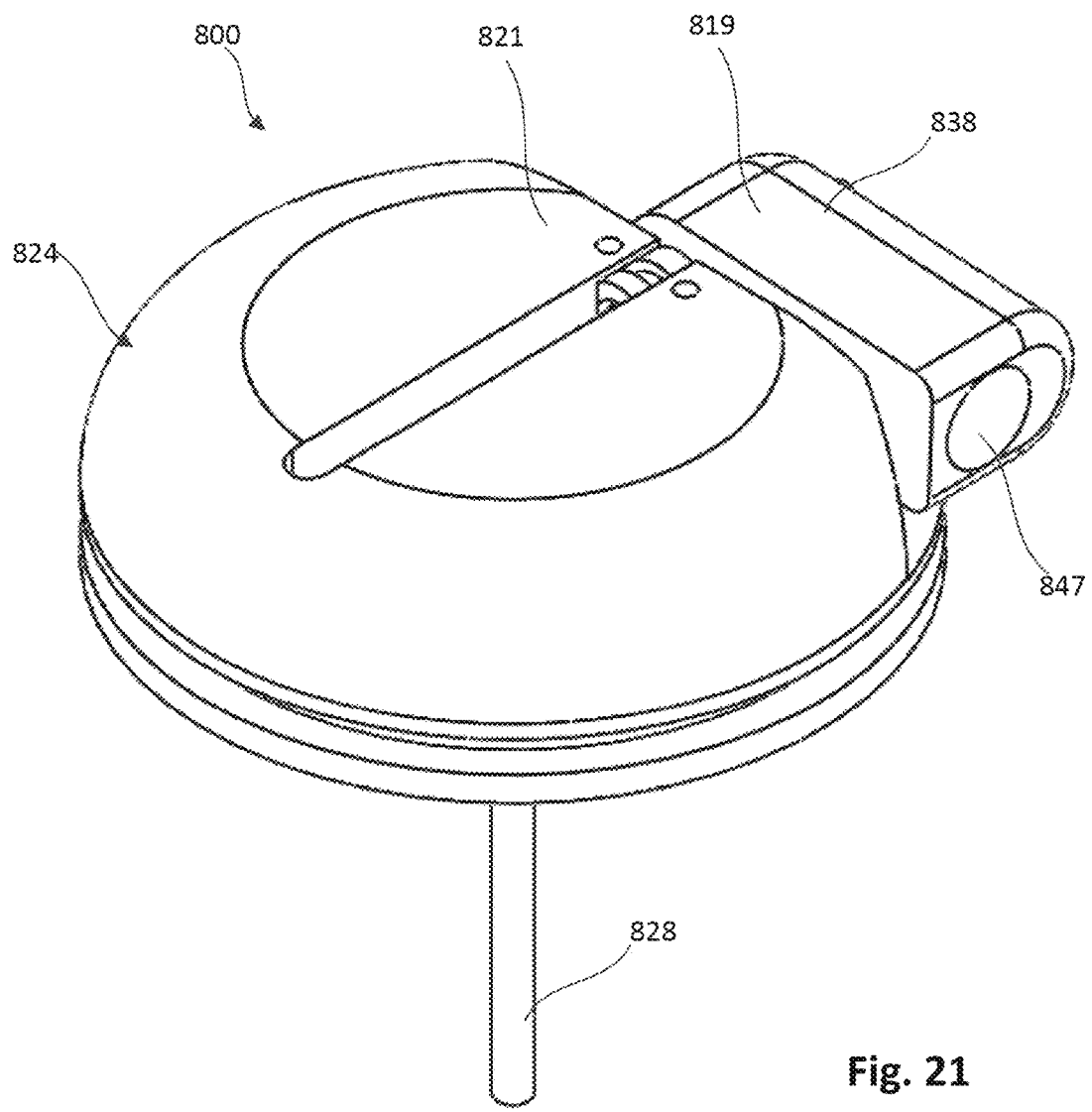
FIG. 21 is a top perspective view of the tether attachment member of FIG. 17 with the access arm shown in a second position.
Figure 22:
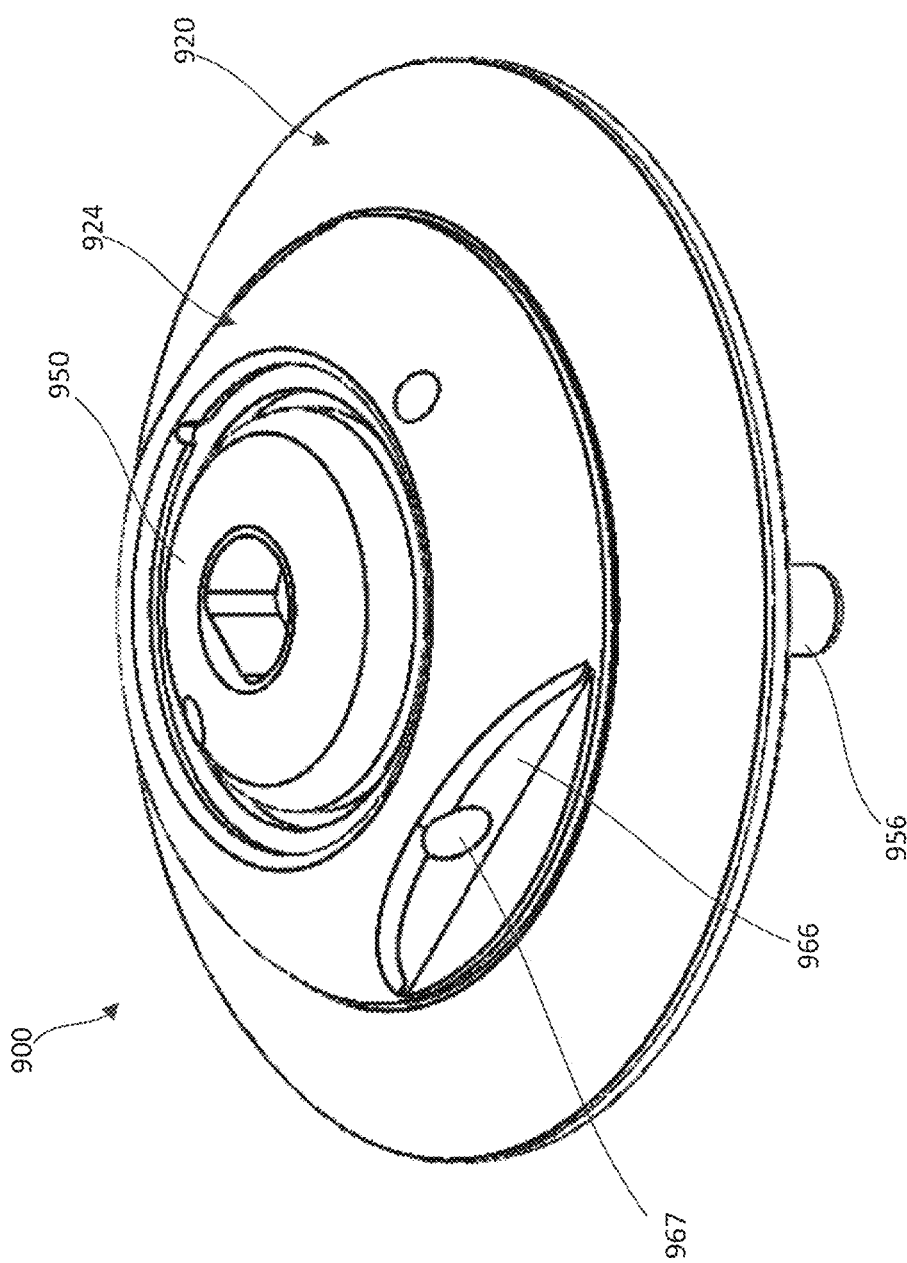
FIG. 22 is a top perspective view of an epicardial anchor device, according to another embodiment.
Figure 23:
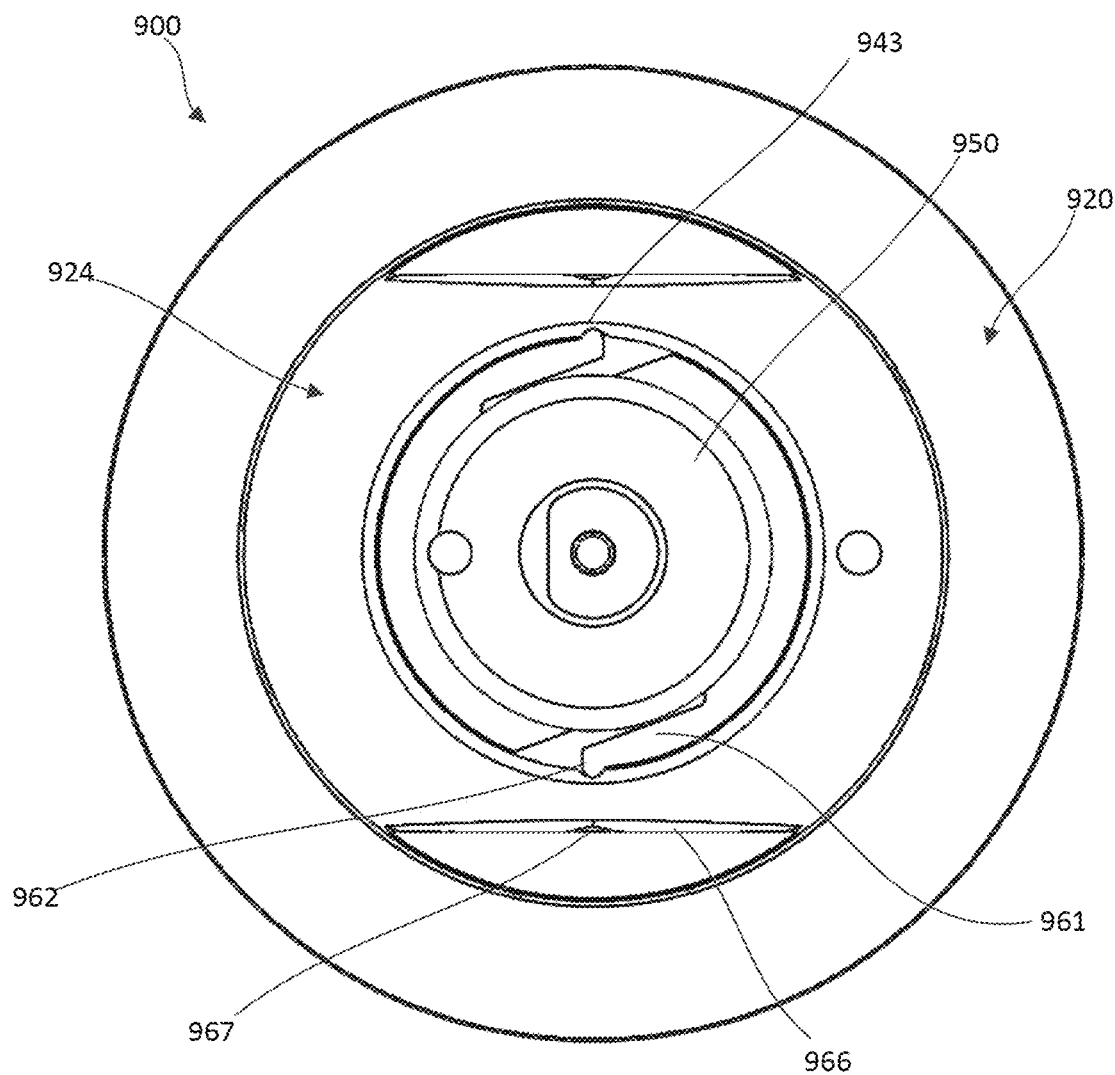
FIG. 23 is a top view of the epicardial anchor device of FIG. 22.
Figure 24:
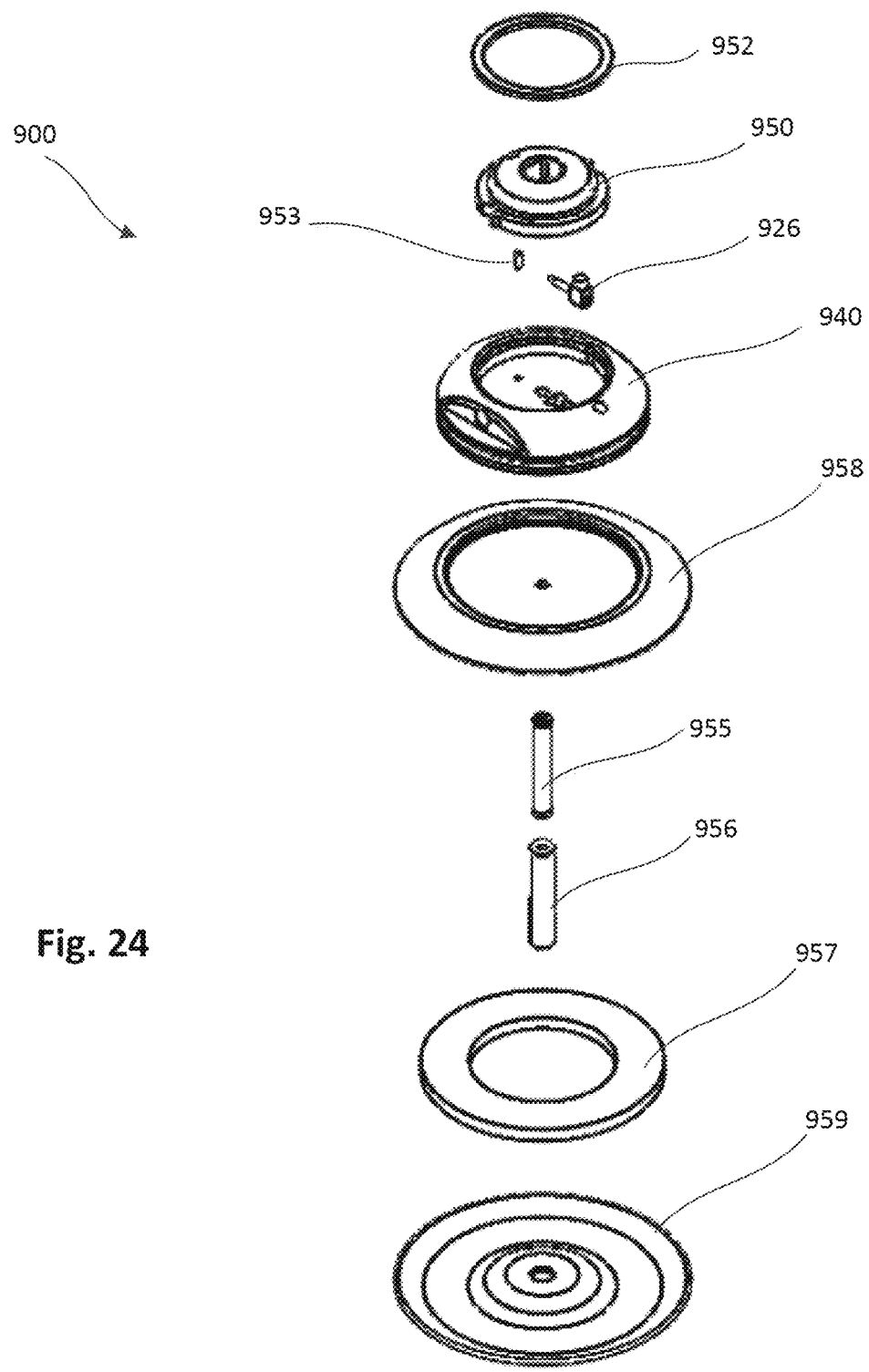
FIG. 24 is an exploded view of the epicardial anchor device of FIG. 22.

The lever arm 838 can be moved (e.g., rotated, pivoted) between a first or open position, as shown, for example, in FIGS. 17 and 18, in which the lever arm 838 extends in a proximal direction from the base member 840, and a second or closed position as shown in FIG. 21, in which a proximal surface 819 of the lever arm 838 is substantially flush with a proximal surface 821 of the base member 840. When the lever arm 838 is in the first or open position, a delivery tool 848 can be coupled to the lever arm 828 as shown in FIGS. 19 and 20. The delivery tool 848 can include a driver 849 shown in FIG. 18 (e.g., a screw driver) that can engage the driver portion 846 of the locking pin 826 to move the locking pin 826 within the locking pin channel 834.

In operation, the tether 828 can be inserted into the tether passageway 835 and extend out of the opening 815 and within the delivery tool 848. The tether 828 can then be tightened to a desired tension. With the tether 828 at the desired tension, the driver 849 of the delivery tool 848 can then move the locking pin 826 from the first position, as shown in FIG. 17 to the second position in which the piercing portion 849 pierces or engages the tether 828, securing the tether 828 to the tether attachment member 824. For example, the driver 849 of the delivery tool 848 can threadably move the locking pin 826 from the first position to the second position. After the tether 828 is secured to the tether attachment member 824, the delivery tool 849 can be removed and the lever arm 838 can be moved to the second or closed position as shown in FIG. 21.

FIGS. 22-30 illustrate an epicardial anchor device according to another embodiment. An epicardial anchor device 900 includes a tether attachment member 924, a pad assembly 920, a tube member 955 and a tube cover member 956. The tether attachment member 924 includes a base member 940, a hub 950, a retaining ring 952, a locking pin assembly 926, and a pin member 953. The locking pin assembly 926 includes a driver portion 946 and a piercing portion 949. The base member 940 defines a circumferential pad channel 942, a retaining channel 951 and a locking pin channel 934. The pad channel 942 can be used to couple the pad assembly 920 to the tether attachment member 924. The retaining channel 951 can receive an outer edge of the retaining ring 952, which is used to retain the hub 950 to the base member 940. The base member 940 also defines cutouts or detents 943, as shown for example, in FIGS. 23, 25 and 30.

The tube member 955 is coupled to the base member 940 and the base member 940, the hub 950 and the tube member 955 collectively define a tether passageway 935 through which a tether (not shown) can be received. The cover member 956 can be formed with a fabric material, such as for example, Dacron®. The tether channel 935 intersects the locking pin channel 934 and is in fluid communication therewith.

The pad assembly 920 includes a top pad portion 958, a bottom pad portion 959 and a filler member 957 disposed therebetween. The top pad portion 958 and the bottom pad portion 959 can each be formed with, for example, a flexible fabric material. The top pad portion 958 and the bottom pad portion 959 can each define a central opening through which the tube member 955 can pass through. A portion of the top pad portion 958 is received within the channel 942 of the base member 940 as shown, for example, in FIGS. 25-27.

Figure 25:
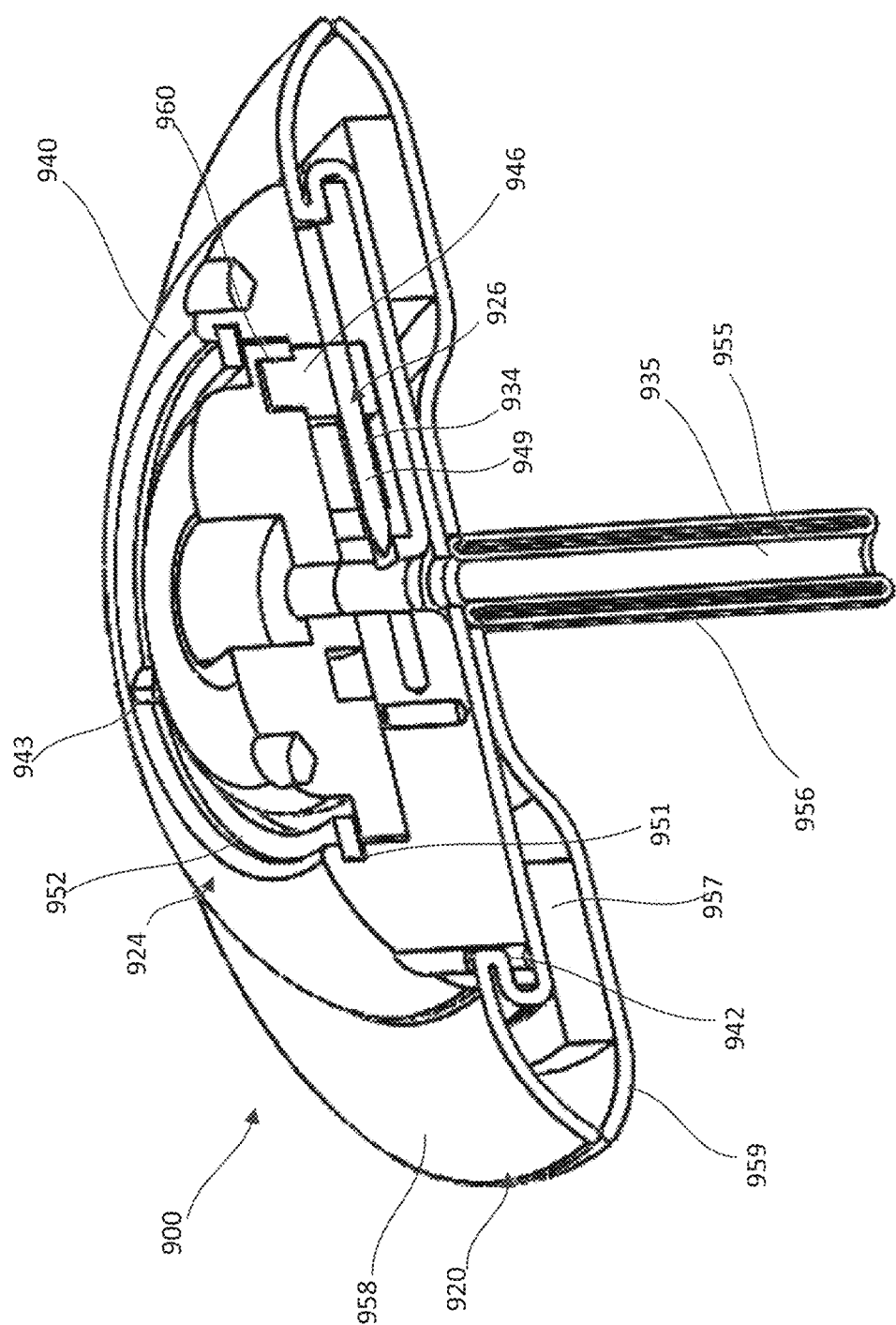
FIG. 25 is a cross-sectional perspective view of the epicardial anchor device of FIG. 22 with a locking pin of the device shown in a first position.
Figure 26:
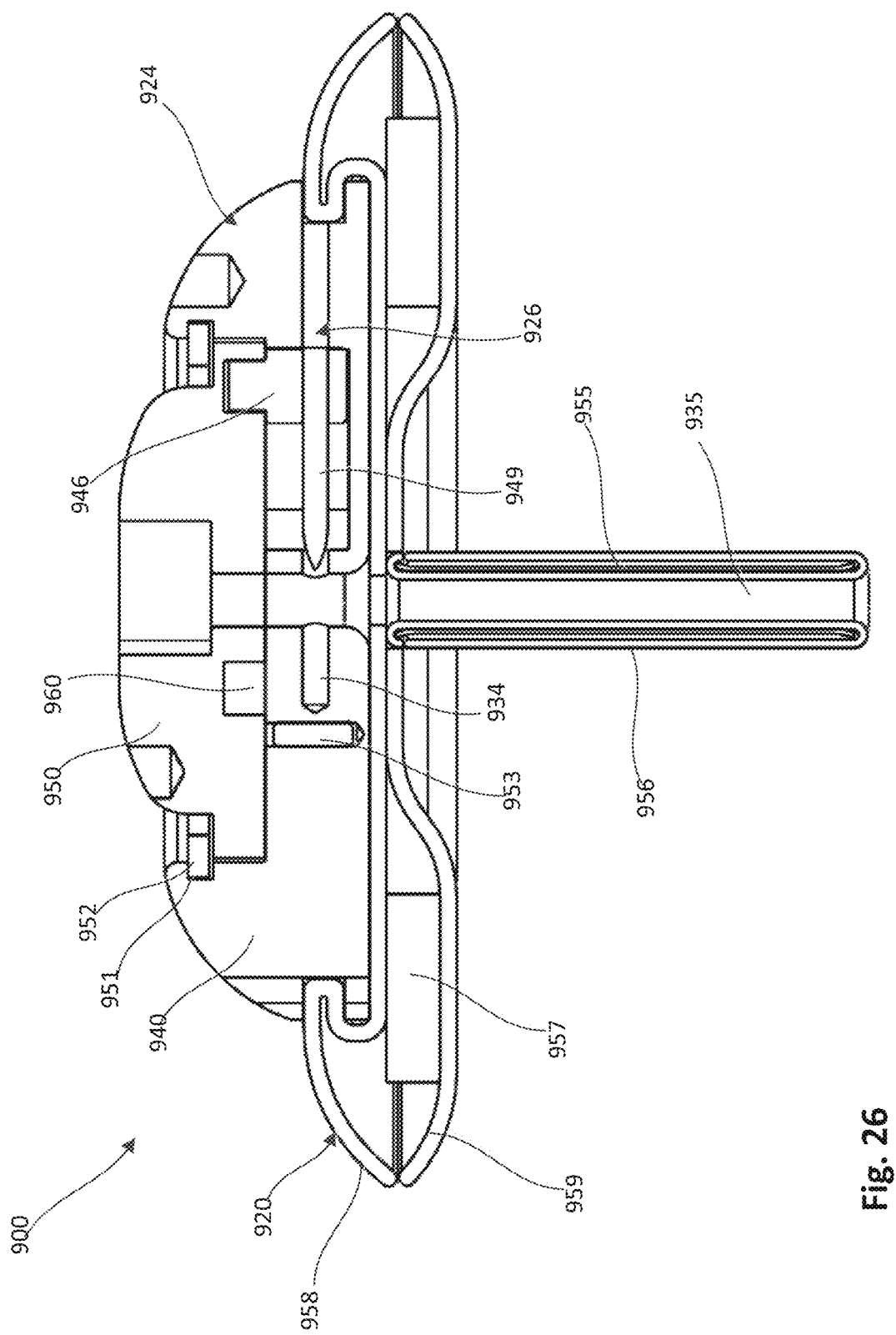
FIG. 26 is a cross-sectional side view of the epicardial anchor device of FIG. 20 with the locking pin of the device shown in the first position.
Figure 27:
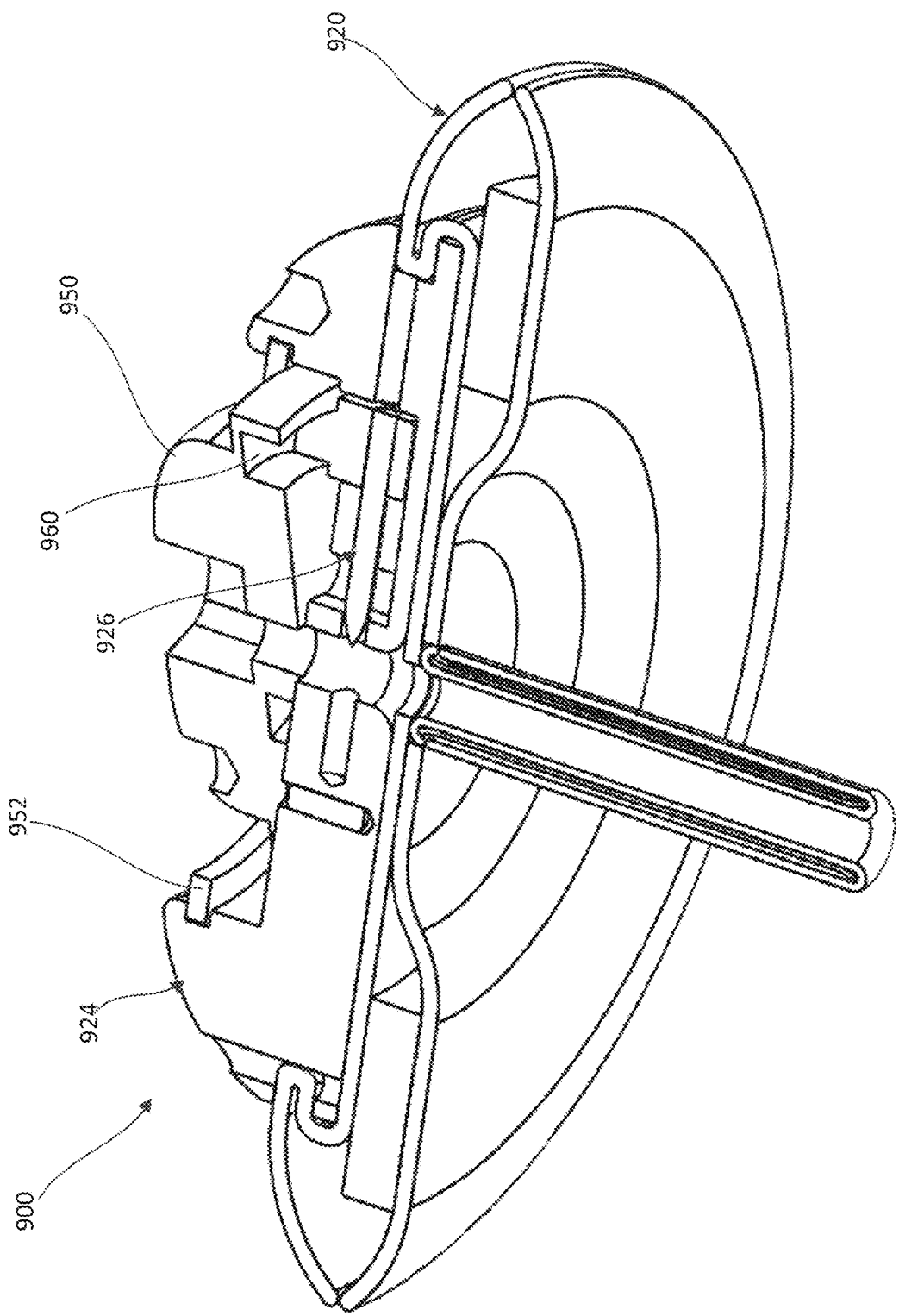
FIG. 27 is a cross-sectional bottom perspective view of the epicardial anchor device of FIG. 22 with the locking pin shown in a second position.
Figure 28:
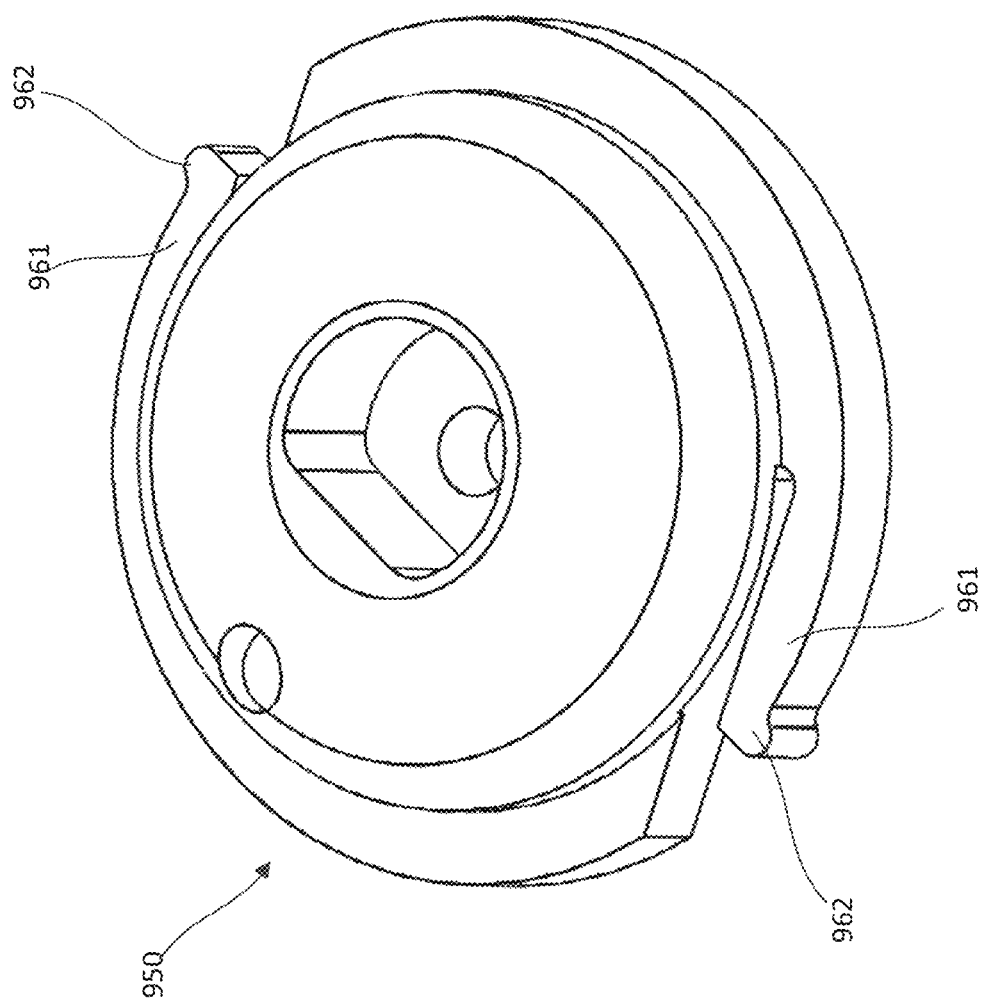
FIGS. 28 and 29 are a top perspective and a bottom perspective view, respectively, of a hub member of the epicardial anchor device of FIG. 22.
Figure 29:
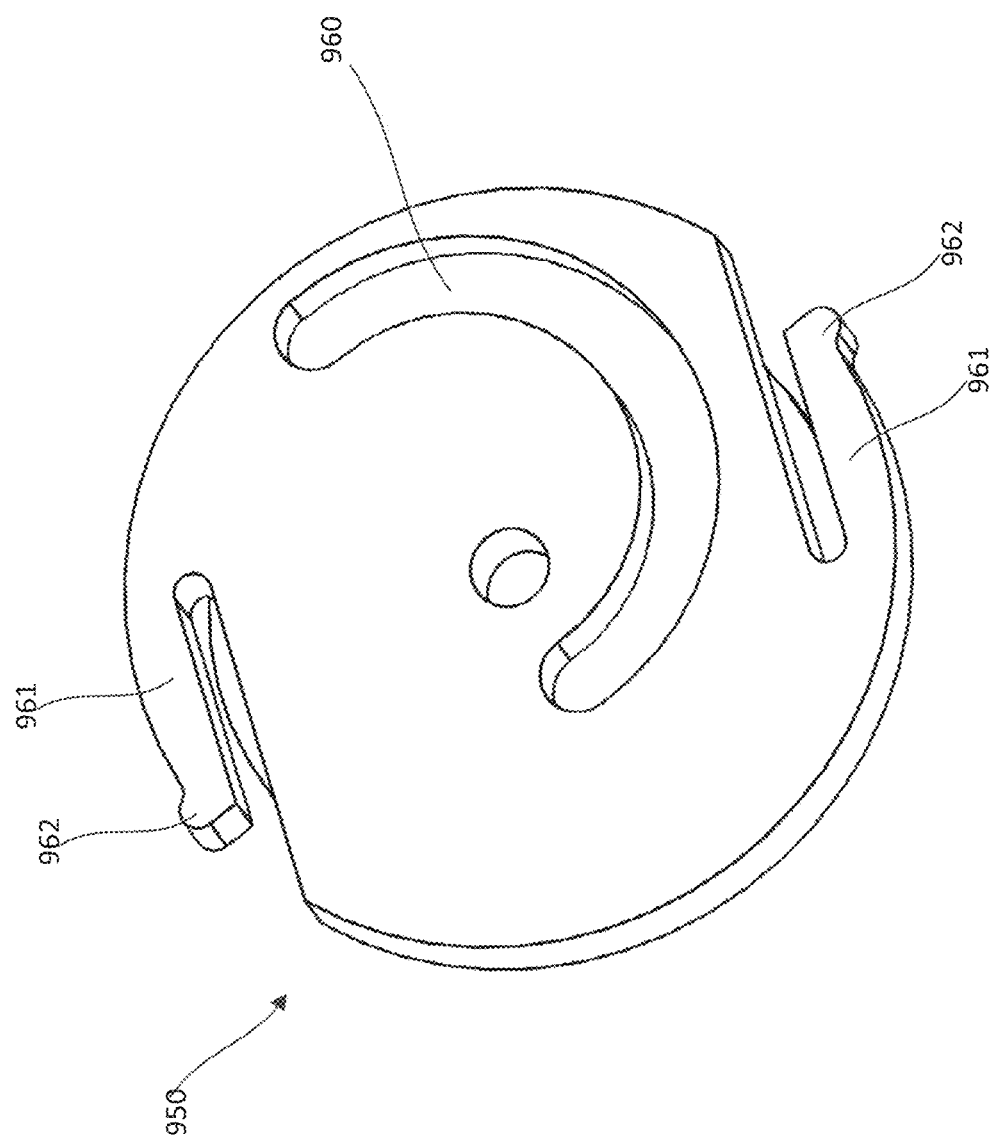
Figure 30:
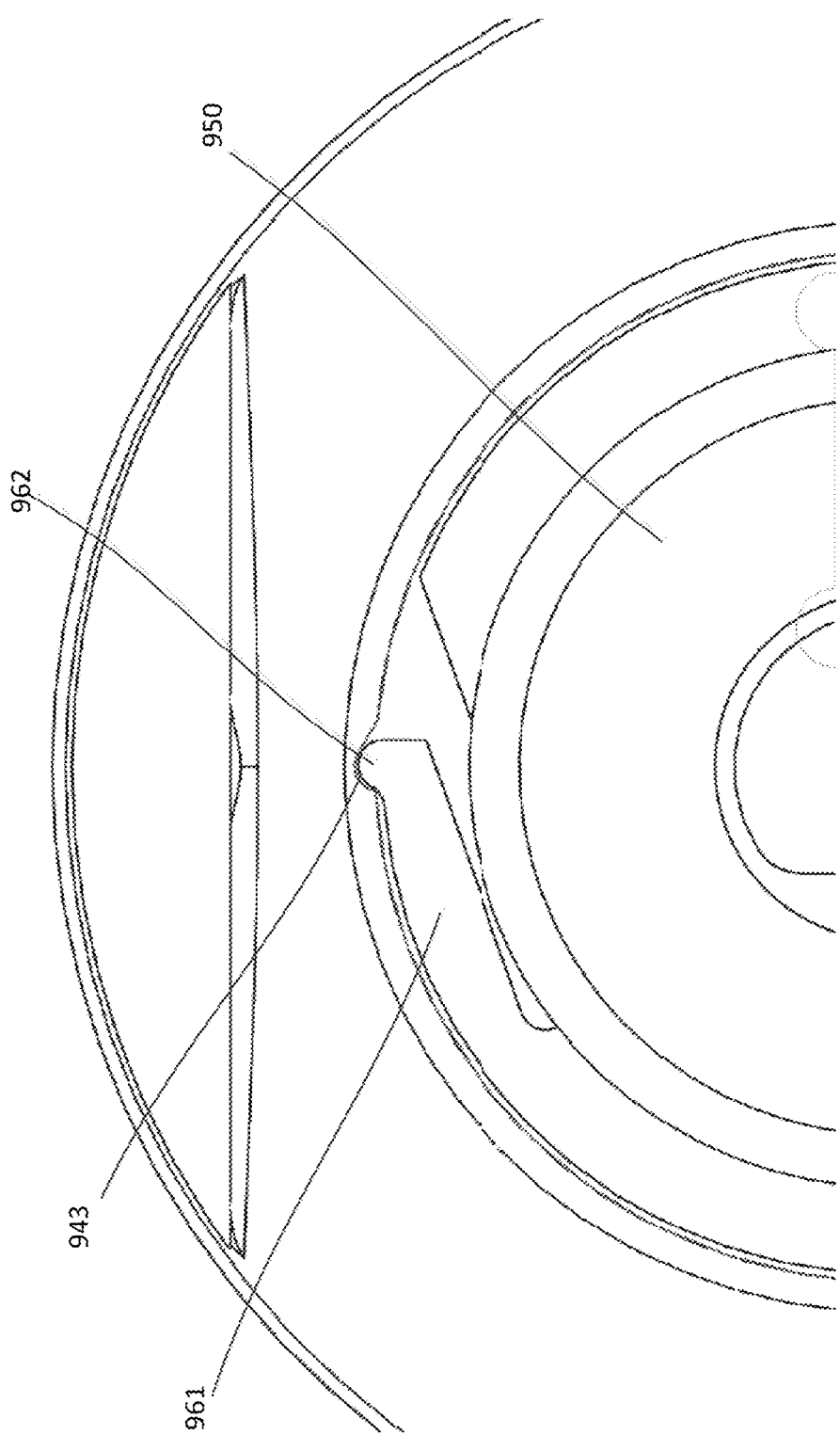
FIG. 30 is an enlarged top view of a portion of the pericardial pad device of FIG. 22.

An outer perimeter portion of the hub 950 is received within the retaining channel 951 such that the hub 950 can rotate relative to the base member 940 to actuate the locking pin assembly 926 as described in more detail below. As shown, for example, in FIGS. 28 and 29, the hub 950 includes arms 961 with protrusions 962. The protrusions 962 can be received within cutouts 943 of the base member 940 and act as a stop or limit to the rotation of the hub 950. The slots 963 defined by the hub 950 enable the arms 961 to flex and allow the protrusions 962 to be moved in and out of the cutouts 943. As shown, for example, in FIGS. 27 and 29 the hub 950 defines a curved channel 960 on a bottom portion of the hub 950. The curved channel 960 is asymmetrical (or spiral) and receives the driver portion 946 of the locking pin assembly 926. As the hub 950 is rotated relative to the base member 940, the hub 950 acts as a cam to move the locking pin assembly 926 linearly within the locking pin channel 934. The locking pin assembly 926 can be moved from a first position in which the piercing portion 949 is disposed outside of the tether passageway 935 as shown in FIGS. 25 and 26, and a second position in which the piercing portion 949 extends through the tether passageway 935 as shown in FIG. 27. The pin member 953 (see, e.g., FIG. 26) can be formed with a metal material that is more radio-opaque than the other components of the anchor device and thus visible to the user (e.g. physician) using conventional imaging modalities to enable the user to confirm that the locking pin assembly 926 has been fully moved to the second position.

In use, when the locking pin assembly 926 is in the first position, a tether (not shown) coupled to, for example, a prosthetic mitral valve and extending through a puncture site in the ventricular wall of a heart can be inserted through the tether passageway 935. The hub 950 can then be rotated 180 degrees to move the locking pin assembly 926 linearly within the locking pin channel 934 such that the piercing portion 949 extends through the tether passageway 935 and engages or pierces the tether, securing the tether to the tether attachment member 924. For example, when the locking pin is in the first position, the protrusions 962 of the hub 950 are each disposed within one of the cutouts 943 of the base member 940 (i.e., a first protrusion is in a first cutout, and a second protrusion is in a second cutout). The hub 950 can then be rotated 180 degrees such that the protrusions 962 are moved out of the cutouts 943 of the base member 940 and at the end of the 180 degrees the protrusions 962 are moved into the other of the cutouts 943 of the base member 940 (i.e., the first protrusion is now in the second cutout, the second protrusion is now in the first cutout).

Figure 31:
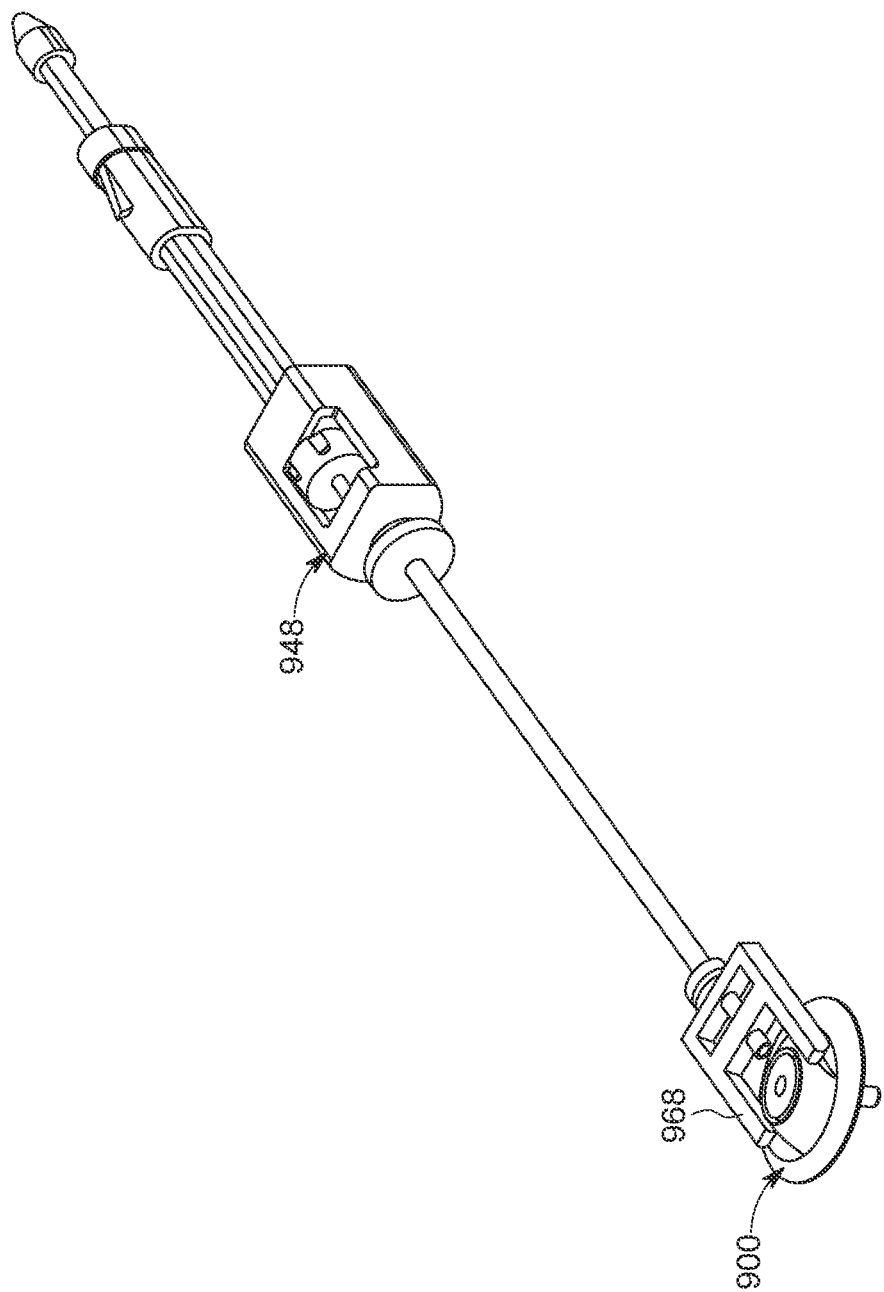
FIG. 31 is a perspective view of the epicardial anchor device of FIG. 22 with a delivery device coupled thereto.

The base member 940 can also include cutout sections 966 and define side openings 967 (see, e.g., FIGS. 22 and 23) that can be used to couple a delivery device to the epicardial anchor device 900. For example, FIG. 31 illustrates a delivery device 948 having coupling arms 968 and coupling pins (not shown) extending inwardly from the arms 968. The side openings 967 can receive the coupling pins and the cutout sections 966 can be engaged by the coupling arms 968.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The invention claimed is:

1. A method of securing a prosthetic heart valve to a heart, the method comprising:
    inserting a portion of a tether into a tether passageway defined by a tether attachment member, the tether extending from the prosthetic heart valve while the prosthetic heart valve is positioned within a native heart valve of the heart;
    disposing the tether attachment member adjacent an opening in a ventricular wall of the heart from which the tether extends; and
    actuating the tether attachment member such that a locking pin disposed within a locking pin channel defined by the tether attachment member intersects the tether passageway and engages a portion of the tether disposed within the tether passageway, securing the tether to the tether attachment member,
    wherein the tether attachment member includes a base member and a lever arm movably coupled to the base member, and actuating the tether attachment member includes moving the lever arm relative to the base member from a first position in which the tether can be inserted into the tether passageway to a second position in which the locking pin intersects the tether passageway and engages the portion of the tether.

2. The method of claim 1, further comprising:
prior to actuating the tether attachment member, adjusting the tension of the tether extending through the tether passageway to a desired tension.

3. A method of securing a prosthetic heart valve to a heart, the method comprising:
inserting a portion of a tether into a tether passageway defined by a tether attachment member, the tether extending from the prosthetic heart valve while the prosthetic heart valve is positioned within a native heart valve of the heart;
disposing the tether attachment member adjacent an opening in a ventricular wall of the heart from which the tether extends; and
actuating the tether attachment member such that a locking pin disposed within a locking pin channel defined by the tether attachment member intersects the tether passageway and engages a portion of the tether disposed within the tether passageway, securing the tether to the tether attachment member,
wherein the tether attachment member includes a base member and a hub rotatably coupled to the base member, a portion of the locking pin being received within a locking pin channel defined by the hub, and actuating the tether attachment member includes rotating the hub relative to the base member such that the hub moves the locking pin linearly within the locking pin channel from a first position in which the locking pin is spaced from the tether passageway to a second position in which the locking pin intersects the tether passageway and engages the portion of the tether.

4. The method of claim 3, wherein the base member has a retaining channel, and the hub has an outer perimeter portion received within the retaining channel.

5. The method of claim 3, wherein the base member and the hub each define at least a portion of the tether passageway.

6. The method of claim 3, wherein the locking pin channel intersects the tether passageway at a transverse angle and is in fluid communication therewith.

7. The method of claim 3, wherein a bottom portion of the hub defines a curved channel in which a driver portion of the locking pin is received.

8. The method of claim 7, wherein rotating the hub relative to the base member moves the driver portion of the locking pin along the curved channel.

9. The method of claim 3, further comprising contacting the ventricular wall with a pad coupled to the tether attachment member so that the pad is disposed between the ventricular wall and the tether attachment member.

10. The method of claim 3, wherein a tube member is coupled to the base member, the tube member defining a portion of the tether passageway.

11. The method of claim 10, wherein a cover member is disposed over the tube member.

12. The method of claim 3, wherein the base member defines a detent configured to receive therein a protrusion on the hub to limit the rotation of the hub relative to the base member.

13. The method of claim 3, further comprising engaging coupling arms of a delivery device to cutout sections in the base member.

14. The method of claim 13, further comprising engaging coupling pins extending from the coupling arms of the delivery device with side openings defined within the cutout sections of the base member.

15. The method of claim 14, further comprising adjusting the tension of the tether using the delivery device while the delivery device is engaged to the base member.

16. The method of claim 15, wherein actuating the tether attachment member is performed after adjusting the tension of the tether.

17. The method of claim 3, further comprising:
prior to actuating the tether attachment member, adjusting the tension of the tether extending through the tether passageway to a desired tension.

* * * * *